United States Patent
Chu et al.

(12) 
(10) Patent No.: US 6,666,853 B2
(45) Date of Patent: Dec. 23, 2003

(54) LOW PROFILE ADAPTOR FOR USE WITH A MEDICAL CATHETER

(75) Inventors: Michael S. H. Chu, Brookline, MA (US); Laddvanh Bouphavichith, Clinton, MA (US)

(73) Assignee: SciMed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 10/107,948

(22) Filed: Mar. 27, 2002

(65) Prior Publication Data

US 2003/0187424 A1 Oct. 2, 2003

(51) Int. Cl.[7] .................. A61M 25/16; A61M 5/00; A61M 5/178; A61M 5/32
(52) U.S. Cl. .................. 604/533; 604/178; 604/250; 604/164.02
(58) Field of Search ................ 604/523–537, 604/246, 250, 178, 164.07

(56) References Cited

U.S. PATENT DOCUMENTS

| | | |
|---|---|---|
| 4,473,369 A | 9/1984 | Lueders et al. |
| 4,557,261 A | 12/1985 | Rügheimer |
| 4,774,944 A | 10/1988 | Mischinski |
| 4,834,712 A | 5/1989 | Quinn et al. |
| 4,863,438 A | 9/1989 | Gauderer et al. |
| 4,944,732 A | 7/1990 | Russo |
| 5,007,900 A | 4/1991 | Picha et al. |
| 5,026,352 A | 6/1991 | Anderson |
| 5,071,405 A | 12/1991 | Piontek et al. |
| 5,100,394 A | 3/1992 | Dudar et al. |
| 5,112,310 A | 5/1992 | Grobe |
| 5,158,569 A | 10/1992 | Strickland et al. |
| 5,167,627 A | 12/1992 | Clegg et al. |
| 5,259,399 A | 11/1993 | Brown |
| 5,267,983 A | 12/1993 | Oilschlager et al. |
| 5,290,250 A | 3/1994 | Bommarito |
| 5,358,488 A | 10/1994 | Suriyapa |
| 5,488,949 A | 2/1996 | Kreifels et al. |
| 5,549,657 A | 8/1996 | Stern et al. |
| 5,720,734 A | 2/1998 | Copenhaver et al. |
| 5,836,924 A | 11/1998 | Kelliher et al. |
| 6,095,997 A | 8/2000 | French et al. |

FOREIGN PATENT DOCUMENTS

EP 976418 2/2000

*Primary Examiner*—Brian L. Casler
*Assistant Examiner*—Roz Ghafoorian
(74) *Attorney, Agent, or Firm*—Kriegsman & Kriegsman

(57) ABSTRACT

A low profile adaptor for use with a medical catheter, such as a gastrostomy feeding tube. In one embodiment, the adaptor comprises a body, a clamp and a cap. The body includes a base portion and a sleeve portion, the base portion being dimensioned to engage the skin of a patient and having a transverse bore, the sleeve portion extending upwardly from the base portion and having a longitudinal slot aligned with the transverse bore and a transverse slot intersecting the longitudinal bore. The clamp, which is slidably mounted on the base portion and across the transverse slot of the sleeve, comprises a plate having a transverse opening. The transverse opening has a wide region alignable with the longitudinal bore and correspondingly dimensioned and a narrow region alignable with the longitudinal bore. In use, a medical catheter is inserted up through the base portion and the sleeve portion, including the transverse opening of the clamp situated within the sleeve, and is then inverted over the top edge of the sleeve. The cap is then threadingly mounted on top of the sleeve so as to secure the inverted end of the catheter to the exterior of the sleeve. The cap is provided with an opening through which access to the catheter may be gained. By aligning the wide region or the narrow region of the clamp with the longitudinal bore of the sleeve, one can open or close, respectively, the catheter to the passage of fluids therethrough.

31 Claims, 18 Drawing Sheets

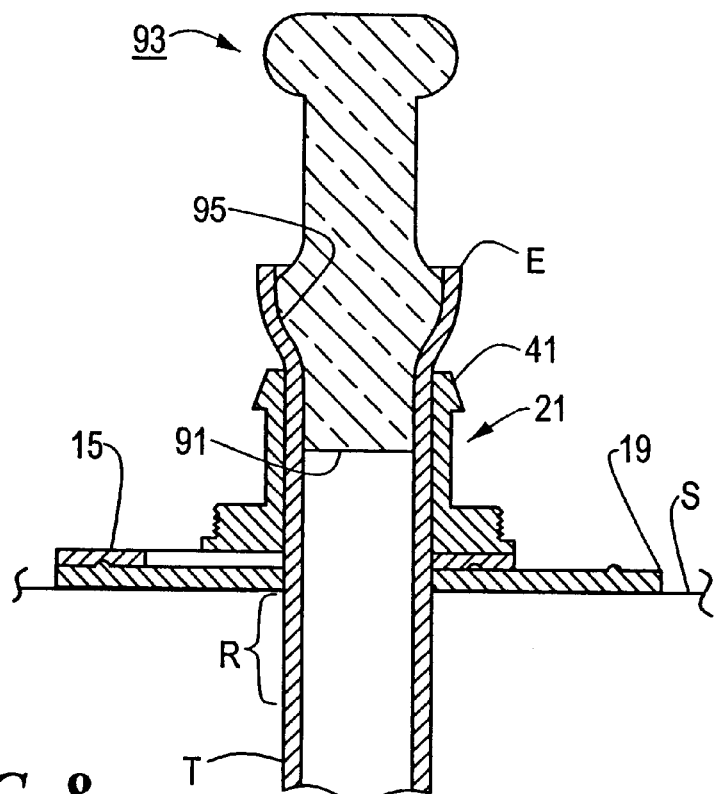
FIG. 8
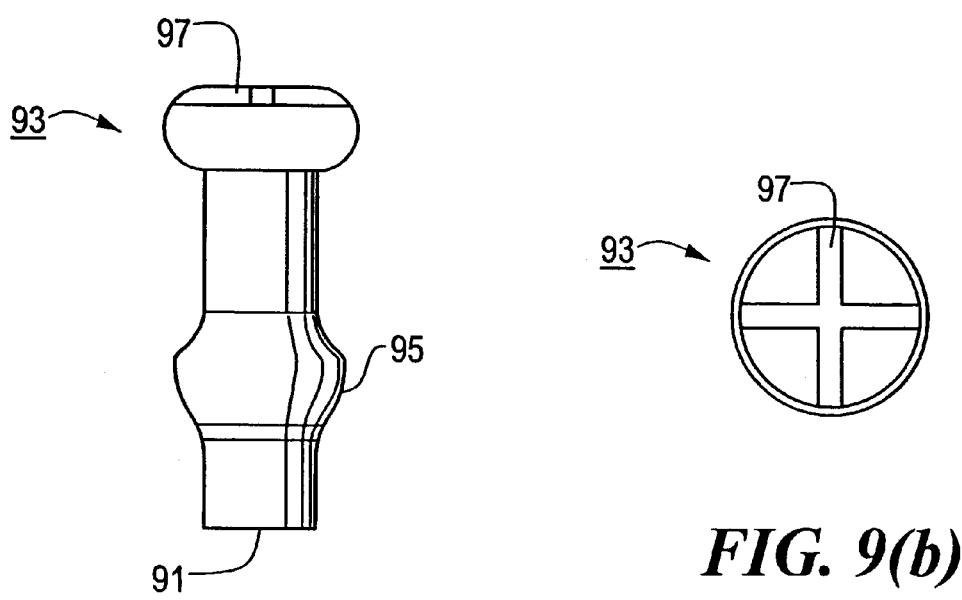
FIG. 9(a)  FIG. 9(b)

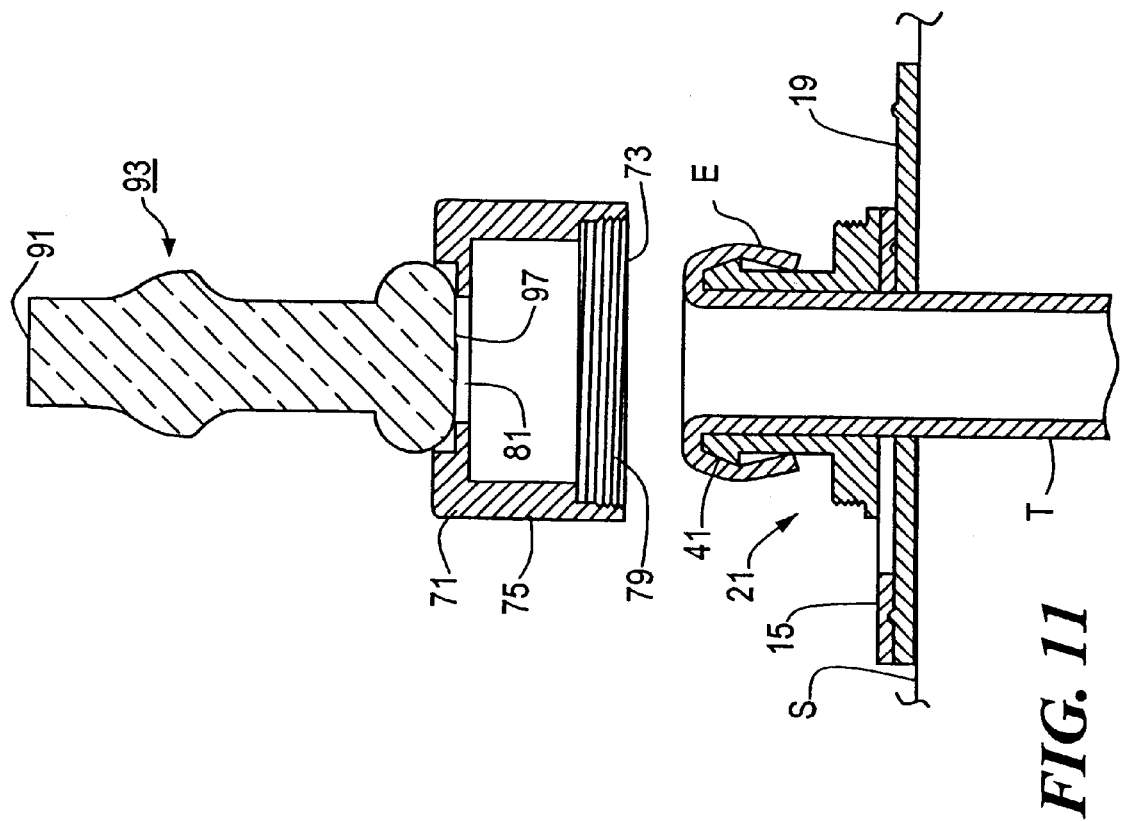
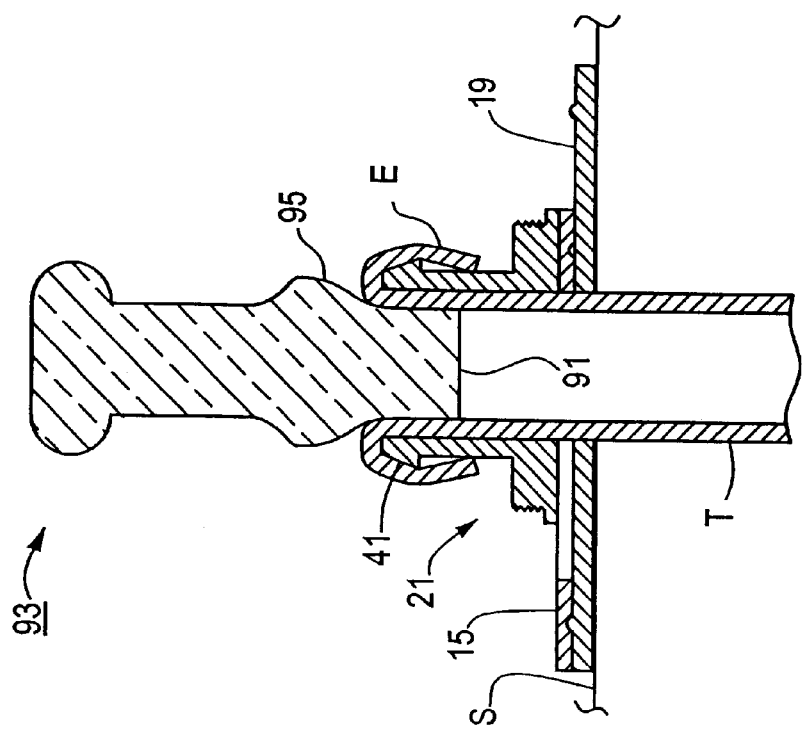
FIG. 11
FIG. 10

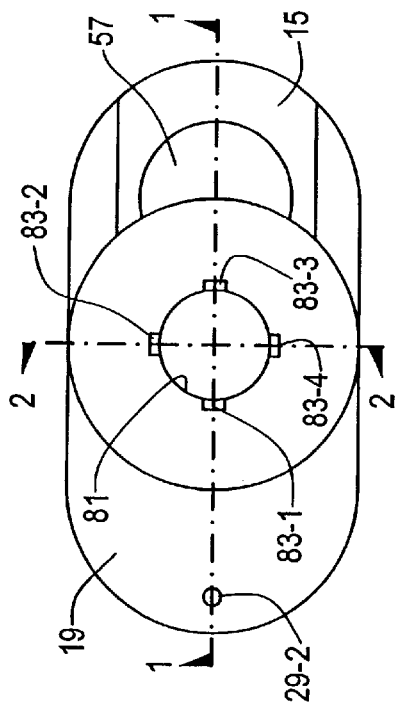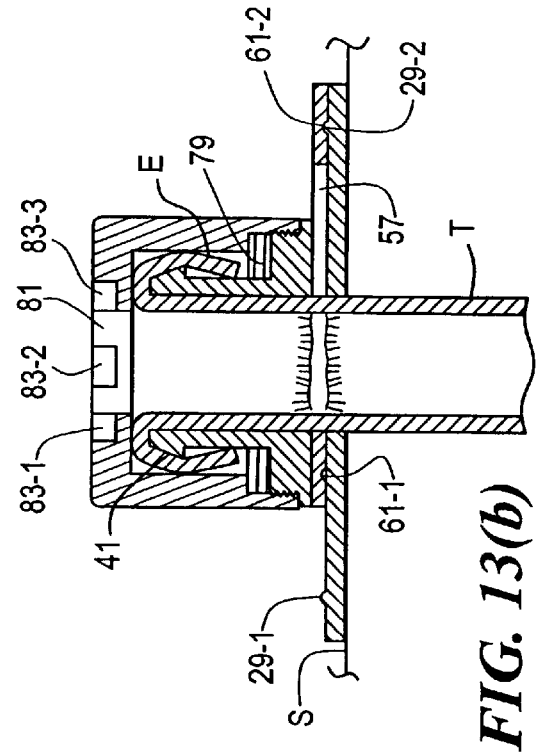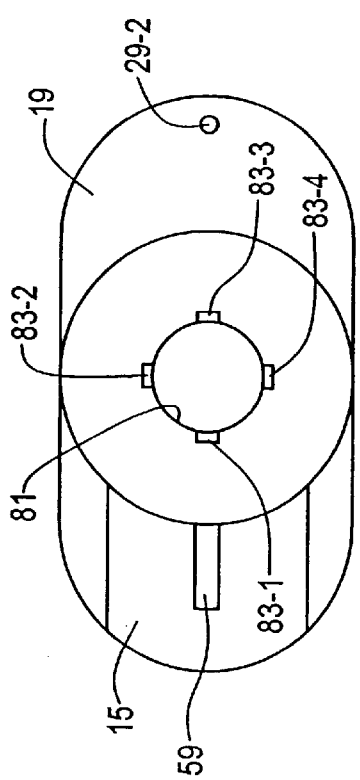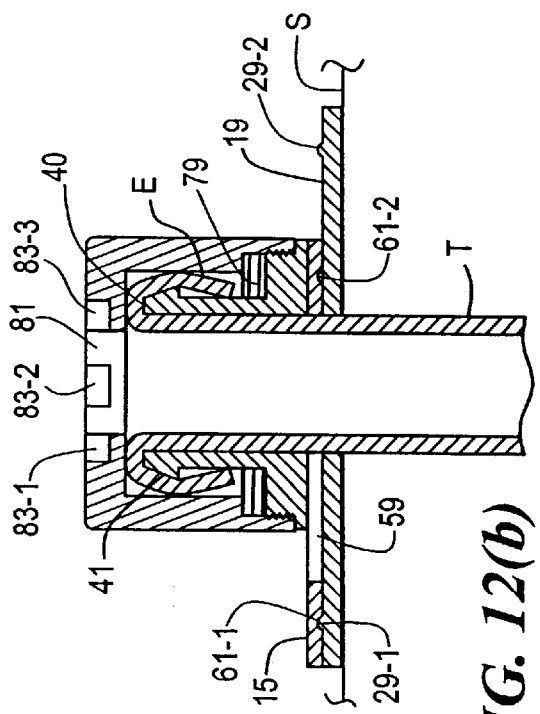
FIG. 12(a)
FIG. 12(b)
FIG. 13(a)
FIG. 13(b)

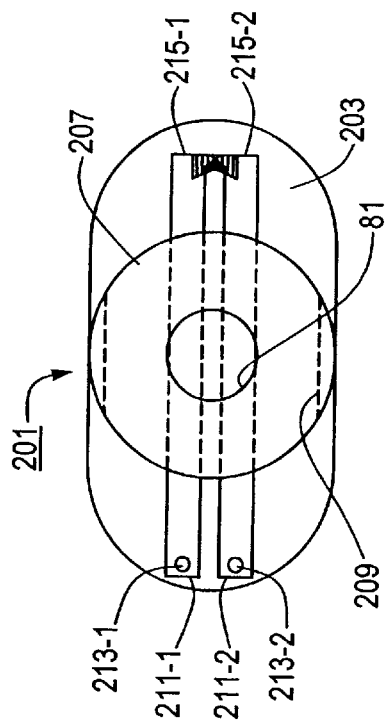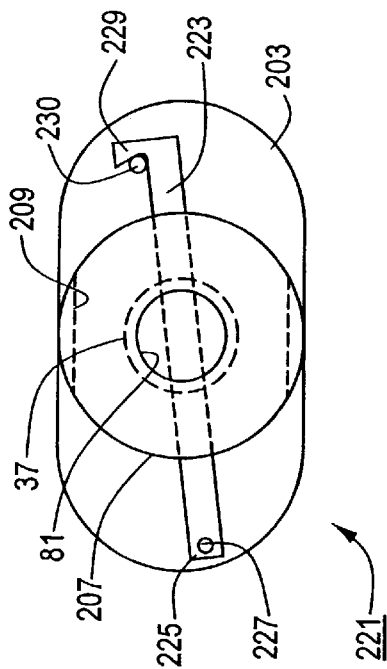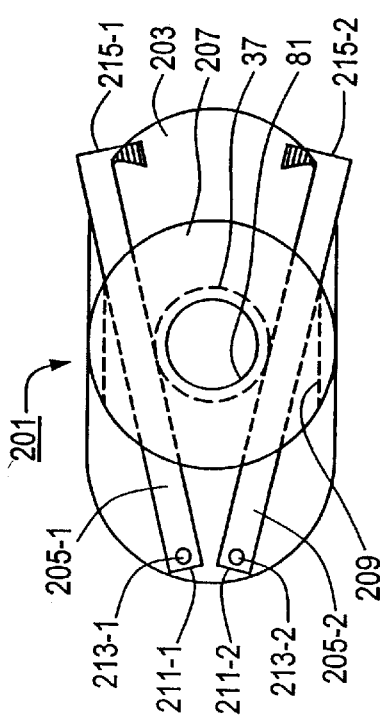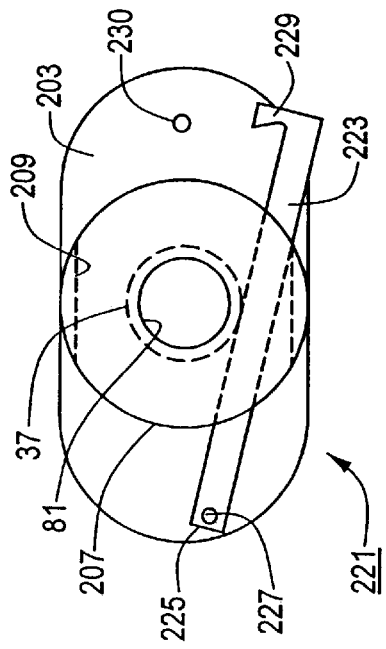

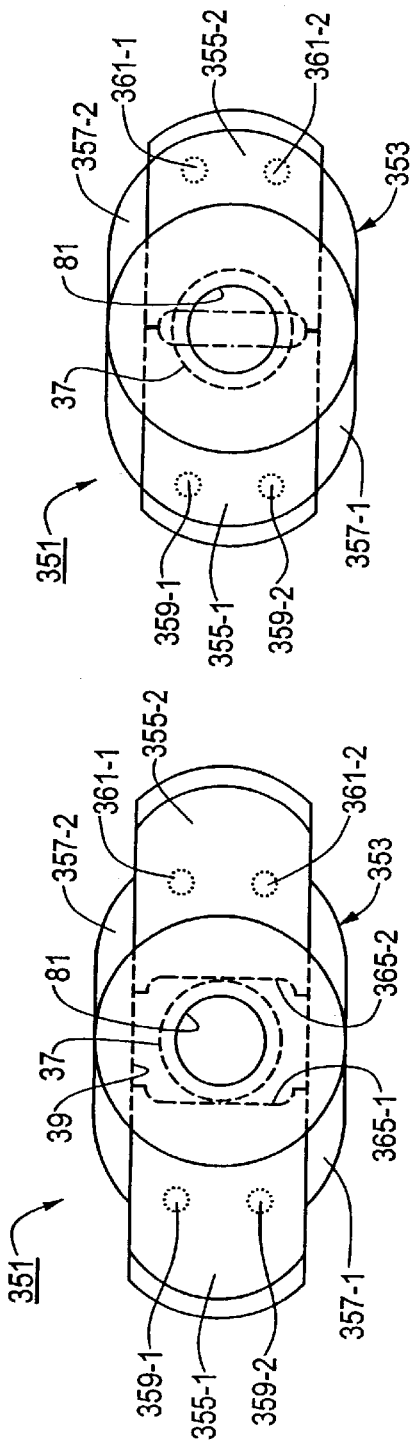
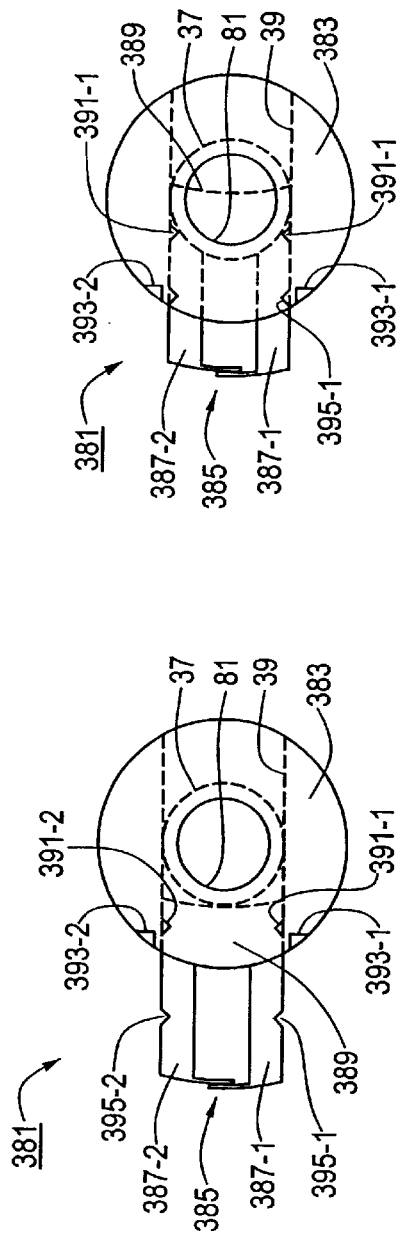

LOW PROFILE ADAPTOR FOR USE WITH A MEDICAL CATHETER

BACKGROUND OF THE INVENTION

The present invention relates generally to medical catheters, such as gastrostomy feeding tubes, and relates more particularly to low profile adaptors well-suited for use with medical catheters.

Certain patients are unable to take food and/or medications transorally due to an inability to swallow. Such an inability to swallow may be due to a variety of reasons, such as esophageal cancer, neurological impairment and the like. Although the intravenous administration of food and/or medications to such patients may be a viable short-term approach, it is not well-suited for the long-term. Accordingly, the most common approach to the long-term feeding of such patients involves gastrostomy, i.e., the creation of a feeding tract or stoma between the stomach and the upper abdominal wall. Feeding is then typically performed by administering food through a feeding tube that has been inserted into the feeding tract, with the distal end of the feeding tube extending into the stomach and being retained therein by an internal anchor or bolster and the proximal end of the feeding tube extending through the abdominal wall.

Although gastrostomies were first performed surgically, most gastrostomies are now performed using percutaneous endoscopy. In one type of percutaneous endoscopic gastrostomy (PEG) technique, the distal end of an endoscope is inserted into a patient's mouth and is passed through the esophagus into the stomach. After distension of the stomach by inflation, an entry site on the abdomen is identified and an incision can be made. A needle, with an outer cannula, is inserted through the entry site across the abdominal and gastric walls. While keeping the cannula in place, the needle is removed, and a flexible wire is passed through the cannula into the stomach and into a snare loop extended from the distal end of the endoscope. The endoscopic snare loop is then used to grasp the wire, the cannula is released, and the endoscope and wire are withdrawn through the esophagus and mouth of the patient. A silicone gastrostomy feeding tube, the distal end of which is attached to a silicone, dome-shaped internal bolster, is then secured to the wire and is pulled from its proximal end through the esophagus and into the stomach until the internal bolster engages the stomach wall and the feeding tube extends through the stomach and abdominal walls, with the proximal end of the feeding tube extending approximately one foot beyond the abdominal wall. (Over a period of several days following implantation of the feeding tube, a stable stoma tract forms around the feeding tube between the gastric and abdominal walls.)

With the internal bolster in place against the gastric wall, an external bolster is typically secured to the feeding tube to engage the abdomen so as to prevent longitudinal movement of the feeding tube within the stoma tract Additionally, a "Y-port" adapter is typically attached to the proximal end of the feeding tube, the Y-port adapter being adapted to receive a pair of connector tips through which food and/or medications may be dispensed. In addition, a detachable locking clip is typically secured to the feeding tube at a point between the external bolster and the Y-port adapter to prevent gastric fluids from escaping through the proximal end of the feeding tube when the feeding tube is not in use.

Alternative techniques for implanting gastrostomy feeding tubes using percutaneous endoscopic gastrostomy are disclosed in U.S. Pat. No. 5,112,310, inventor Grobe, which issued May 12, 1992, and U.S. Pat. No. 5,167,627, inventors Clegg et al., which issued Dec. 1, 1992, both of which are incorporated herein by reference.

Although gastrostomy feeding tubes of the type described above work well for their intended purpose, many active patients find the nearly one foot length of tubing that extends externally to be unwieldy, difficult to conceal and susceptible to being inadvertently pulled on. As can readily be appreciated, these conditions are potential sources of physical and/or psychological trauma to the patient. Consequently, a variety of low-profile replacement tube assemblies (also referred to in the art as low-profile replacement PEG devices) have been designed for implantation within the stoma tract following the removal of an initially-implanted gastrostomy feeding tube. Such replacement assemblies are referred to as being "low-profile" because they are considerably more compact externally than the above-described initially-implanted gastrostomy feeding tube assemblies.

An example of a low-profile replacement PEG device is disclosed in U.S. Pat. No. 4,944,732, inventor Russo, which issued Jul. 31, 1990, and which is incorporated herein by reference. The low-profile replacement PEG device of said patent comprises a deformable, conical tip portion having at least one side aperture therethrough, a tube portion which extends rearwardly from the tip portion, a fitting portion on the rear end of the tube portion, a removable valve portion in the fitting portion and a flange portion which extends outwardly from the fitting portion. The device is adapted to be installed in a patient so that the tube portion extends through a pre-established stoma with the tip portion located in the patient's stomach and with the fitting portion and the flange portion engaging the skin of the patient adjacent the stoma The deformable tip portion of the above-described low-profile replacement PEG device functions as an internal bolster to anchor its associated tube portion in a patient's stomach. To implant and/or remove the aforementioned tube portion from a patient's stomach, an obturator or similar device is typically inserted through the tube portion and is used to elongate or otherwise deform the tip portion in such a way as to permit the tip portion to fit through the stoma. Removal of the obturator from the tip portion then permits the tip portion to expand to its original shape for anchoring.

Another type of low-profile replacement PEG device uses an inflatable balloon, instead of a deformable tip portion, as an internal bolster to retain the distal end of its associated tube within a patient's stomach. To implant such a device in a patient, the inflatable balloon is deflated, the distal end of the tube portion is inserted through the stoma, and the balloon is then inflated. To remove the implanted device from a patient, the balloon is deflated and the tube is then withdrawn from the stoma Further examples of low-profile replacement PEG devices are disclosed in U.S. Pat. No. 4,863,438, inventors Gauderer et al., which issued Sep. 5, 1989; and U.S. Pat. No. 5,720,734, inventors Copenhaver et al., which issued Feb. 24, 1998, both of which are incorporated herein by reference.

Although low-profile replacement PEG devices are less awkward and bulky than initially-implanted gastrostomy tube assemblies, the use of such low-profile replacement PEG devices suffers from its own set of shortcomings. One such shortcoming is that the implantation of a low-profile replacement PEG device must be preceded by the removal of an intially-implanted gastrostomy tube. Such removal typically involves pulling on the proximal end of the gastrostomy tube until the internal bolster fails and is drawn through the stoma. As can readily be appreciated, such a procedure can be quite painful to the patient and can result in damage to the stoma, thereby delaying when the replacement device can be implanted.

Another shortcoming of many low-profile replacement PEG devices is that such devices typically do not last as long as initially-implanted gastrostomy tube assemblies (most commonly due to failure of their internal anchoring mechanisms or due to clogging or other failure of their valve mechanisms) and, therefore, must be replaced more frequently than is the case with initially-implanted gastrostomy tube assemblies.

Still another shortcoming of many low-profile replacement PEG devices is that such devices are typically not adjustable in length. This can be problematic because there is often an appreciable variation in stoma length from patient to patient. Consequently, it is typically necessary, after removal of the initially-implanted tube and prior to implantation of the replacement device, to measure the length of the stoma and then to select a replacement device having an appropriate length. As can readily be appreciated, this approach requires that there be made available an inventory of replacement devices of varying lengths.

In order to avoid the aforementioned shortcomings of low-profile replacement PEG devices while, at the same time, avoiding the above-described problems associated with having a gastrostomy tube extend externally for a substantial length, there have recently been devised a number of adaptors designed for use in converting an initally-implanted gastrostomy tube into a low-profile PEG device. One such adaptor is disclosed in U.S. Pat. No. 5,549,657, inventors Stern et al., which issued Aug. 27, 1996, and which is incorporated herein by reference. According to said patent, an adaptor is disclosed therein that is designed for use with a gastrostomy feeding tube which has been inserted by means of conventional endsocopic procedures and which has been cut to a desired length by a surgeon. The adaptor is said to comprise an anti-reflux valve assembly having a stem which can be plugged into the open end of the feeding tube. The valve assembly is said to contain a seal which functions as a one-way valve to prevent reflux of gastric contents but which permits the introduction of feeding solution into the feeding tube. A clamp is placed around the feeding tube and the valve stem and is locked into place to secure the valve assembly to the feeding tube at a location flush with the patient's skin. A silicone cover is placed around the clamp to protect the patient from skin irritation caused by the clamp and also to protect the clamp and valve assembly from contaminants.

Although the aforementioned adaptor favorably addresses some of the problems discussed above, the present inventors have identified certain shortcomings associated therewith. One such shortcoming is that the clamp of said adaptor is quite small and, therefore, is difficult to manipulate. Moreover, to insert the valve stem down into the gastrostomy feeding tube and then to attach the clamp around the gastrostomy tube against the valve stem, one must allow for a sufficient externally-extending length to be left in the gastostomy tube so that one can grasp the gastrostomy tube at a point distal to where the valve stem and the clamp are coupled to the tube. (Otherwise, the gastrostomy tube may be pushed completely into the patient, for example, as the valve stem is pushed down into the tube.) This extra length of externally-disposed tubing, however, precludes the clamp from resting flush against the patient when the internal bolster is flush against the stomach. Consequently, either the adaptor is positioned a short distance from the skin, thereby rendering it higher in profile than it otherwise would be, or the distal end of the tube extends a short distance into the stomach, possibly interfering with stomach function.

Another shortcoming is that the clamp has a tendency to pinch the proximal end of the gastrostomy tube at those points where the male and female sections of the clamp are joined. Such pinching, over time, has a tendency to cause the tube to tear. In addition, once the clamp is closed, it cannot be re-opened; consequently, one cannot remove and re-attach the valve stem and the clamp from the proximal end of the gastrostomy feeding tube. Accordingly, once the clamp has been closed, one cannot adjust the length of the gastrostomy feeding tube nor can one clean the valve stem or the proximal end of the feeding tube to remove any accumulated debris therewithin. Moreover, one cannot simply eliminate the clamp from the aforementioned adaptor since, in the absence of the clamp, the valve stem, which has a barb-type fitting, can rather easily be pulled out of the feeding tube (i.e., with about a 5 pound pulling force).

Still another shortcoming with the aforementioned adaptor is that the valve assembly of the subject adaptor relies upon the use of a silicone gasket having a Y-shaped slot through which a cannula is typically inserted to deliver food and/or medications. However, such a silicone gasket, after repeated insertions of the cannula therethrough, has a tendency to tear or to otherwise fail to act reliably as a one-way valve. Consequently, because the adaptor cannot easily be disconnected from the gastrostomy feeding tube once connected thereto, replacement of a worn gasket requires the removal and replacement of the gastrostomy feeding tube as well.

Still yet another shortcoming with the aforementioned adaptor is that it possesses a relatively small lumen through which fluid may pass. In addition, due to its manner of operation, the valve tends to get clogged over time, further restricting fluid flow.

SUMMARY OF THE INVENTION

It is an object of the present invention to provide a novel low profile adaptor designed for use with a medical catheter, such as a gastrostomy feeding tube.

It is another object of the present invention to provide a low profile adaptor as described above that overcomes at least some of the problems described above in connection with existing PEG devices, in general, and low profile PEG devices, in particular.

Therefore, according to one aspect of the invention, there is provided a low profile adaptor well-suited for use with a medical catheter, such as a gastrostomy feeding tube, said adaptor comprising (a) a sleeve, said sleeve having a longitudinal bore up through which the proximal end of the medical catheter may be inserted; (b) means for securing the medical catheter to said sleeve; and (c) means for alternately opening and closing the medical catheter to the passage of fluid therethrough.

In a preferred embodiment, the adaptor comprises a body, a clamp and a cap. The body includes a base portion and a sleeve portion, the base portion being dimensioned to engage the skin of a patient and having a transverse bore, the sleeve portion extending upwardly from the base portion and having a longitudinal slot aligned with the transverse bore and a transverse slot intersecting the longitudinal bore. The clamp, which is slidably mounted on the base portion and across the transverse slot of the sleeve, comprises a plate having a transverse opening. The transverse opening has a wide region alignable with the longitudinal bore and correspondingly dimensioned and a narrow region also alignable with the longitudinal bore. In use, a medical catheter is inserted up through the base portion and the sleeve portion, including up through the transverse opening of the clamp situated within the sleeve, and is then inverted over the top edge of the sleeve and across a barb formed on the exterior of the sleeve. The cap is then threadingly mounted on top of the sleeve so as to secure the inverted end of the catheter to the exterior of the sleeve. The cap is provided with an opening through which access to the catheter may be gained. By aligning the wide region or the narrow region of the clamp with the longitudinal bore of the sleeve, one can open or close, respectively, the catheter to the passage of fluids therethrough.

According to another aspect of the invention, there is provided a low profile adaptor well-suited for use with a medical catheter, the medical catheter having a proximal end, said adaptor comprising (a) a body, said body having a base and a sleeve, said base having a transverse bore, said sleeve extending upwardly from said base and having a longitudinal bore and a transverse slot, said longitudinal bore being aligned with said transverse bore of said base, said transverse slot intersecting said longitudinal bore, said transverse bore of said base and said sleeve being appropriately dimensioned to permit a medical catheter to be inserted up through said transverse bore of said base and said longitudinal bore of said sleeve and then inverted over the top of said sleeve; (b) a clamp mounted on said base and movable within said transverse slot between a first position in which said clamp transversely compresses to closure the medical catheter and a second position in which said clamp does not transversely compress the medical catheter, and (c) means for securing the inverted proximal end of a medical catheter to said sleeve.

The present invention is also directed to combinations of the adaptors described above and medical catheters, such as gastrostomy feeding tubes, secured thereto.

According to still another aspect of the invention, there is provided a method of externally bolstering the proximal end of an implanted medical catheter to a patient, said method comprising the steps of (a) providing a body, said body having a base portion and a sleeve portion, said base portion being dimensioned to engage the patient and having a transverse bore, said sleeve portion extending upwardly from said base and, having a longitudinal bore and a top edge, said longitudinal bore being aligned with said transverse bore; (b) inserting the proximal end of the implanted medical catheter up through said transverse bore of said base and said longitudinal bore of said sleeve; and (c) inverting the proximal end of the implanted medical catheter over the top edge of the sleeve onto the exterior of the sleeve.

As can readily be appreciated, although the adaptors discussed above are described as being low profile adaptors, such adaptors are also suitable for use with medical catheters, such as gastrostomy feeding tubes, that extend externally for several inches. Accordingly, the adaptors of the present invention are not limited to being low profile adaptors.

For purposes of the present specification and claims, relational terms like "top," "bottom," "upper," and "lower" are used to describe the present invention in an context in which the invention is secured to a catheter extending upwardly out of a patient. It is to be understood that, by orienting a patient such that the catheter extends outwardly in a direction other than upwardly, the directionality of the invention will need to be adjusted accordingly.

Additional objects, as well as features and advantages, of the present invention will be set forth in part in the description which follows, and in part will be obvious from the description or may be learned by practice of the invention. In the description, reference is made to the accompanying drawings which form a part thereof and in which is shown by way of illustration various embodiments for practicing the invention. The embodiments will be described in sufficient detail to enable those skilled in the art to practice the invention, and it is to be understood that other embodiments may be utilized and that structural changes may be made without departing from the scope of the invention. The following detailed description is, therefore, not to be taken in a limiting sense, and the scope of the present invention is best defined by the appended claims.

BRIEF DESCRIPTION OF THE DRAWINGS

The accompanying drawings, which are hereby incorporated into and constitute a part of this specification, illustrate various embodiments of the invention and, together with the description, serve to explain the principles of the invention. In the drawings wherein like reference numerals represent like parts:

FIG. 8 is a section view showing the insertion of the bottom end of a tool down into the proximal end of the gastrostomy feeding tube of FIG. 6 so as to cause said proximal end to flare outwardly;

FIGS. 9(a) and 9(b) are front and enlarged top views, respectively, of the tool of FIG. 8;

FIG. 10 is a section view showing the proximal end of the gastrostomy feeding tube of FIG. 7 folded over the barbed portion of the body;

FIG. 11 is a section view showing the top end of the tool of FIGS. 9(a) and 9(b) being used to screw the cap of FIG. 1 over the combination of the proximal end of the gastrostomy feeding tube and the body shown in FIG. 10;

FIGS. 12(a) and 12(b) are top and section views, respectively, of the adaptor of FIG. 1 in a fully assembled state secured to the proximal end of an implanted gastrostomy feeding tube, with the clamp in an open position;

FIG. 13(a) is a top view of the adaptor of FIG. 1 in a fully assembled state secured to the proximal end of an implanted gastrostomy feeding tube, with the clamp in a closed position;

FIGS. 13(b) and 13(c) are section views of the adaptor and implanted gastrostomy feeding tube of FIG. 13(a) taken along lines 1—1 and 2—2, respectively, the compression of the gastrostomy feeding tube in FIG. 13(b) being depicted by wrinkles therein;

FIGS. 17(a) and 17(b) are top views, in an open position and in a closed position, respectively, of a fifth embodiment of a low profile adaptor constructed according to the teachings of the present invention for use with a medical catheter;

FIGS. 18(a) and 18(b) are top views, in an open position and in a closed position, respectively, of a sixth embodiment of a low profile adaptor constructed according to the teachings of the present invention for use with a medical catheter.

FIGS. 22(a) and 22(b) are top views, in an open position and in a closed position, respectively, of a tenth embodiment of a low profile adaptor constructed according to the teachings of the present invention for use with a medical catheter;

FIGS. 23(a) and 23(b) are top views, in an open position and in a closed position, respectively, of an eleventh embodiment of a row profile adaptor constructed according to the teachings of the present invention for use with a medical catheter;

DETAILED DESCRIPTION OF PREFERRED EMBODIMENTS

Figure 1:
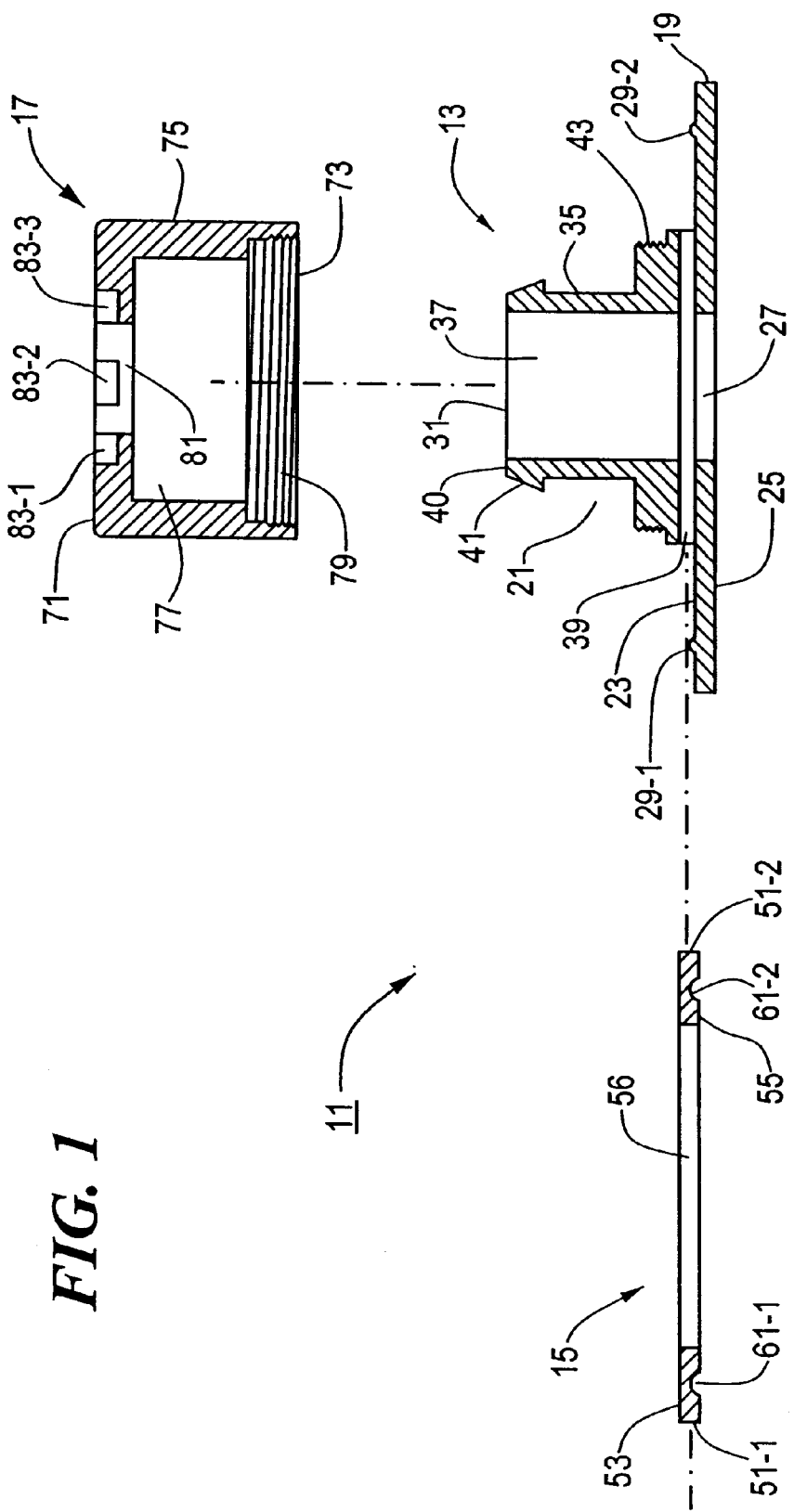
FIG. 1 is an exploded section view of a first embodiment of a low profile adaptor constructed according to the teachings of the present invention for use with a medical catheter, such as a gastrostomy feeding tube.

Referring now to FIG. 1, there is shown an exploded section view of a first embodiment of a low profile adaptor constructed according to the teachings of the present invention for use with a medical catheter, such as a gastrostomy feeding tube, said low profile adaptor being identified generally by reference numeral 11.

Adaptor 11 comprises a body 13, a clamp 15 and a cap 17.

Figure 2:
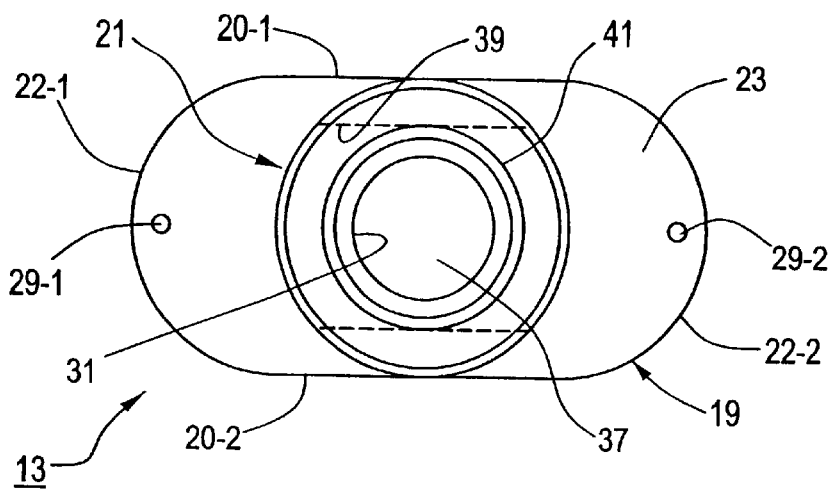
FIG. 2 is a top view of the body shown in FIG. 1, the transverse slot of the body being shown in dotted lines.

Referring now to FIGS. 1 and 2, body 13, which is a unitary structure preferably made of molded medical grade plastic, is shaped to include a base 19 and a sleeve 21. Base 19, which is appropriately sized to be greater than the stoma tract in the patient so as to serve as an external bolster, is a quasi-rectangular member having a pair of straight sides 20-1 and 20-2, a pair of rounded ends 22-1 and 22-2, a top surface 23, a bottom surface 25 and a centrally-disposed transverse bore 27. A pair of detents 29-1 and 29-2 are formed on top surface 23 along its longitudinal centerline, the purpose of detents 29-1 and 29-2 to be discussed below.

Sleeve 21 is an elongated tubular member that extends upwardly from top surface 23, sleeve 21 having an open top end 31, an open bottom end, a generally circular side wall 35, a longitudinal bore 37 and a transverse slot 39. For reasons to be discussed below, the top portion of side wall 35 is shaped to define an upwardly directed external barb 41. For reasons also to be discussed below, an intermediate portion of side wall 35 is shaped to include an external helical thread 43. Longitudinal bore 37 is aligned with transverse bore 27 of base 19 and is substantially equal in diameter thereto. Transverse slot 39, which is formed in the bottom portion of side wall 35 and runs generally parallel to the length of base 19, intersects longitudinal bore 37 for reasons to be discussed below.

Figure 3:
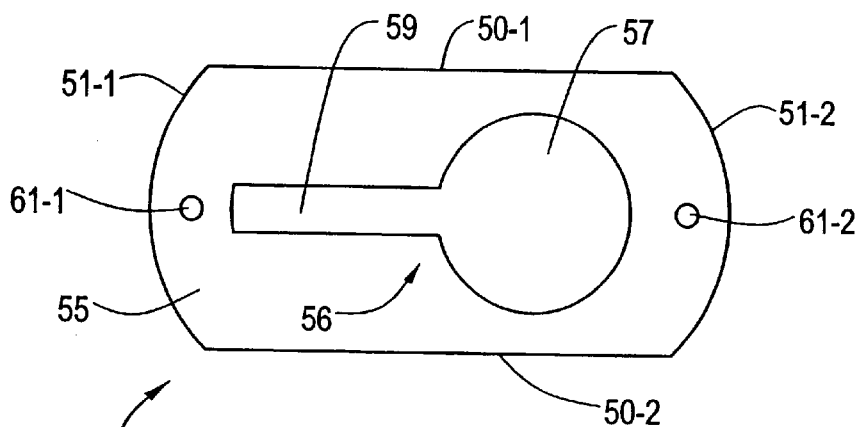
FIG. 3 is a bottom view of the clamp shown in FIG. 1.

Referring now to FIGS. 1 and 3, clamp 15, which is preferably made of molded medical grade plastic, is an elongated, quasi-rectangular slide having a pair of straight sides 50-1 and 50-2, a pair of rounded ends 51-1 and 51-2, atop surface 53, a bottom surface 55, and a transverse opening 56. Transverse opening 56 comprises a wide circular region 57 and a narrow slit region 59. For reasons to become apparent below, wide circular region 57 is substantially equal size to bores 27 and 37 whereas narrow slit region 59 is much smaller than bores 27 and 37. A pair of recesses 61-1 and 61-2 are provided in bottom surface 55 of clamp 15, recess 61-1 being adapted to receive detent 29-1 to maintain clamp 15, when desired, in an open position, recess 61-2 being adapted to receive detent 29-2 to maintain clamp 15, when desired, in a closed position.

Clamp 15 is slidably mounted on base 19 and across slot 39 and is movable between (i) an open position in which circular region 57 is aligned with bores 27 and 37 and detent 29-1 is received in recess 61-1 and (ii) a closed position in which slit region 59 is aligned with bores 27 and 37 and detent 29-2 is received in recess 61-2.

Figure 4:
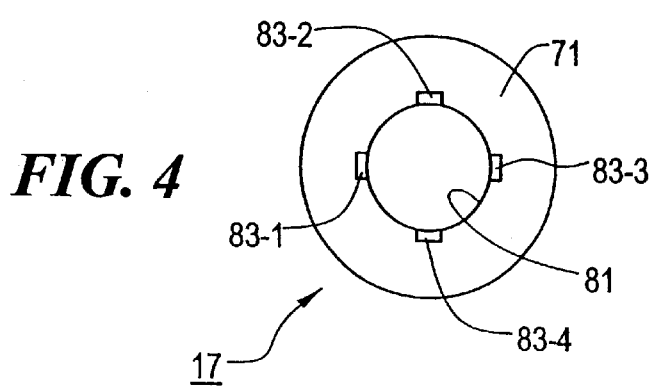
FIG. 4 is a top view of the cap shown in FIG. 1.

Referring now to FIGS. 1 and 4, cap 17, which is a unitary member preferably made of molded medical grade plastic, comprises a top wall 71, an open bottom 73, a circular side wall 75 and a cylindrical cavity 77, cylindrical cavity 77 being circumferentially bounded by side wall 75. The bottom portion of side wall 75 has a decreased cross-sectional thickness, and a helical thread 79 is formed on the inside surface thereof for reasons to be discussed below. A transverse opening 81 having a diameter substantially equal to bore 37 is provided in top wall 71, opening 81 enabling a food and/or medications delivery tube/connector (or a drainage tube/connector) to be inserted therethrough. A plurality of recesses 83-1 through 83-4 equidistantly spaced around the perimeter of opening 81 are provided in the top surface of top wall 71, the purpose of recesses 83-1 through 83-4 to be discussed below.

As will be seen below, cap 17 is appropriately dimensioned so that it may be screwed onto sleeve 21, with thread 79 of cap 17 matingly engaging thread 43 of sleeve 21 and with opening 81 being aligned with bore 37.

Figure 5A:
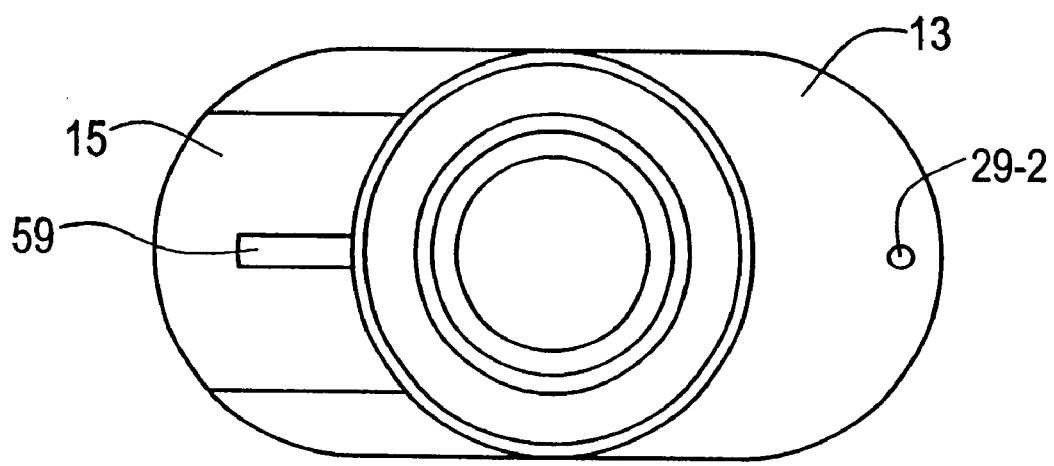
FIGS. 5(a) and 5(b) are top and section views, respectively, of the body and the clamp of FIG. 1 shown in an assembled state, with the clamp in an open position.
Figure 5B:
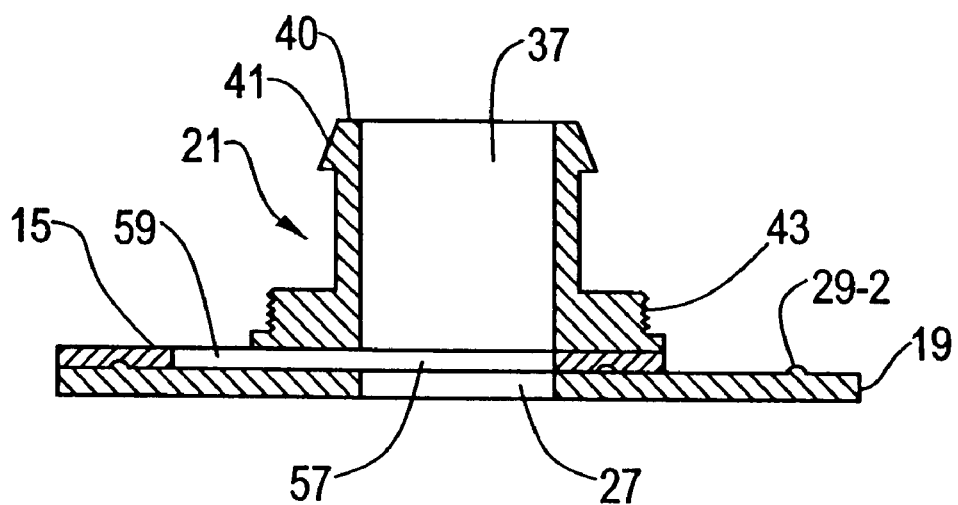
Figure 6:
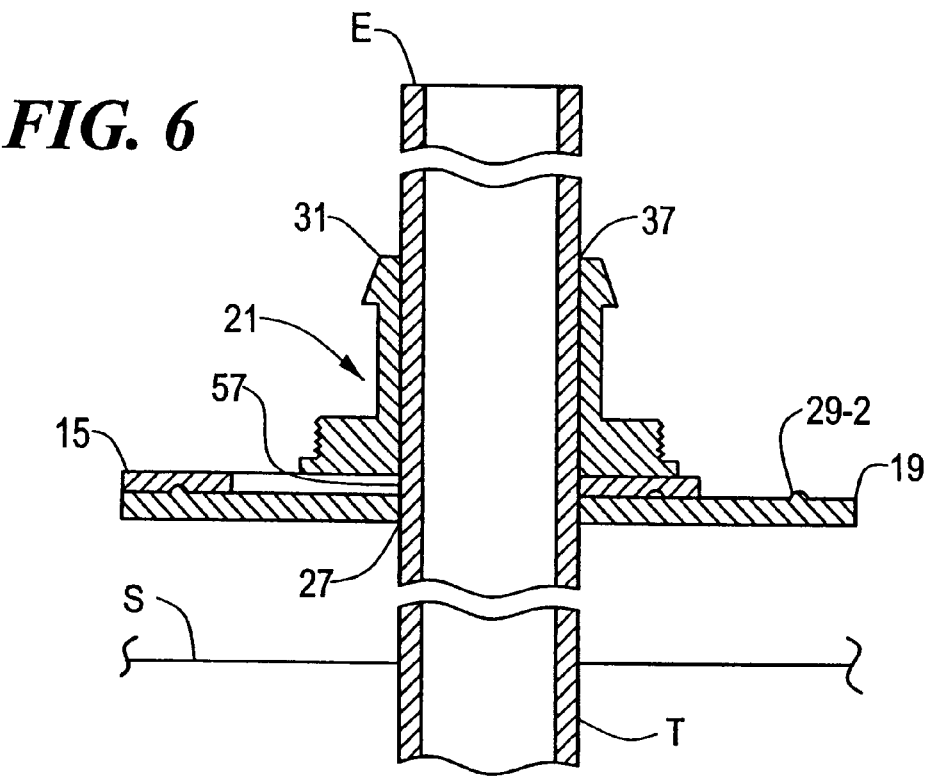
FIG. 6 is a section view showing the proximal end of an implanted gastrostomy feeding tube inserted up through the assembly of FIGS. 5(a) and 5(b)
Figure 7:
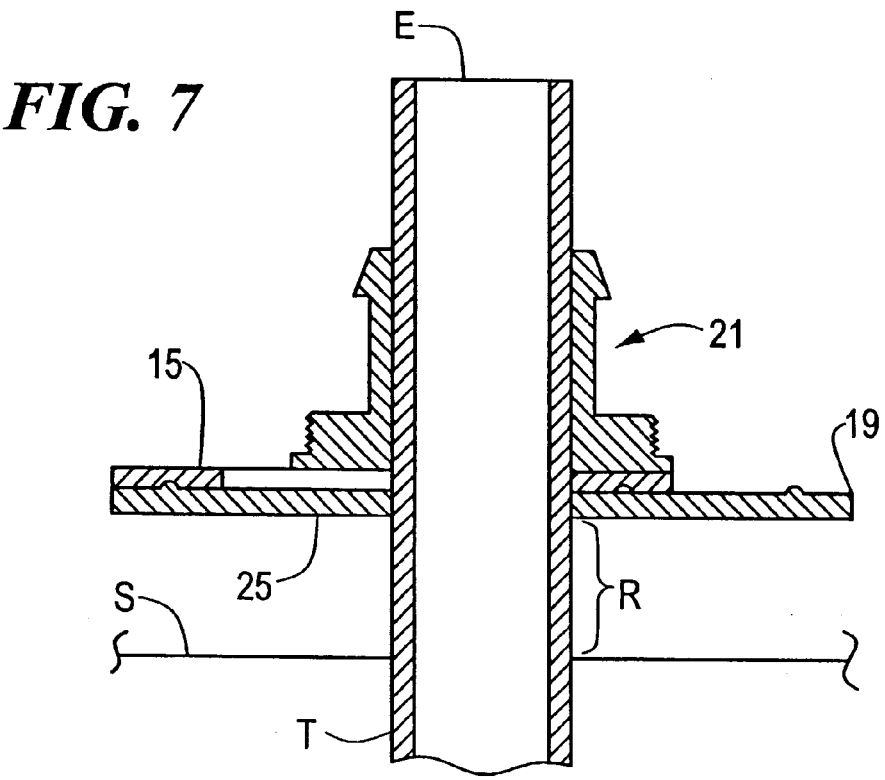
FIG. 7 is a section view showing the implanted gastrostomy feeding tube cut to a desired length following insertion through the assembly of FIGS. 5(a) and 5(b)

The manner in which adaptor 11 may be secured to the proximal end of an implanted medical catheter, such as an implanted gastrostomy feeding tube, will now be discussed. First, as seen in FIGS. 5(a) and 5(b), with cap 17 removed from body 13, clamp 15 is positioned relative to body 13 so that circular region 57 is aligned with bores 27 and 37 and detent 29-1 is received in recess 61-1 (i.e., clamp 15 is placed in its open position). Next, as seen in FIG. 6, the proximal end E of an implanted gastrostomy feeding tube T is inserted up through bore 27, circular region 57, and bore 37, respectively, and extends for a distance beyond open top end 31 of sleeve 21. Next, as seen in FIG. 7, tube T is cut to an appropriate length to permit tube T to be attached to adaptor 11 in a low profile orientation proximate to the patient's skin S while still reserving a tubing length R for stomach expansion and for cleaning under the bottom of base 19.

Next, as seen in FIG. 8, tubing length R is inserted into the patient and bottom surface 25 of base 19 is brought into contact with the patient's skin S. The bottom end 91 of a tool 93 (tool 93 being shown separately in FIGS. 9(a) and 9(b)) is then inserted down into the proximal end E of tube T and into open top end 31 of sleeve 21. Tool 93 has an intermediate portion 95 that flares outwardly from bottom end 91 to a diameter that is greater than the inner diameter of sleeve 21 and that approaches the outer diameter of barb 41. Consequently, the insertion of bottom end 91 of tool 93 into proximal end E of tube T causes proximal end E of tube T to flare outwardly. Next, as seen in FIG. 10, the proximal end E of tube T is then folded over barb 41 of sleeve 21. This may be done simply by rolling the proximal end E of tube T down off intermediate portion 95 of tool 91 using the thumb and forefinger of one hand. As can be appreciated, the engagement of the proximal end E of the tube T by barb 41 inhibits, to a certain degree, withdrawal of the tube T from sleeve 21. Next, as seen in FIG. 11, the top portion 97 of tool 91, which has a shape similar to a Phillips head screwdriver (see FIG. 9(b)), is inserted into recesses 83-1 through 83-4 and is used to screw cap 17 onto sleeve 21.

It should be noted that, although cap 17 and sleeve 21 are secured to one another in the present embodiment by threads 79 and 43, respectively, cap 17 and sleeve 21 could alternatively be removably secured to one another by other suitable means.

FIGS. 12(a) and 12(b) show adaptor 11 in a fully assembled state secured to proximal end E of tube T, with clamp 15 in its open position. As seen best in FIG. 12(b), cap 17 serves to secure tube T against barb 41 and against the top edge 40 of sleeve 21, thereby increasing the grip strength of adaptor 11 to at least 18 pounds. To convey food and/or medications to a patient, a delivery tube/connector is inserted down through opening 81 and into tube T, and the food and/or medications are then dispensed therethrough. It is to be noted that the compression of tube T by cap 17 against sleeve 21 creates a tight seal between the delivery tube/connector and tube T. When the dispensing of the food and/or medications is complete, the delivery tube/connector is withdrawn from tube T and opening 81, and clamp 15 is moved from its open position to its closed position.

Figure 13C:
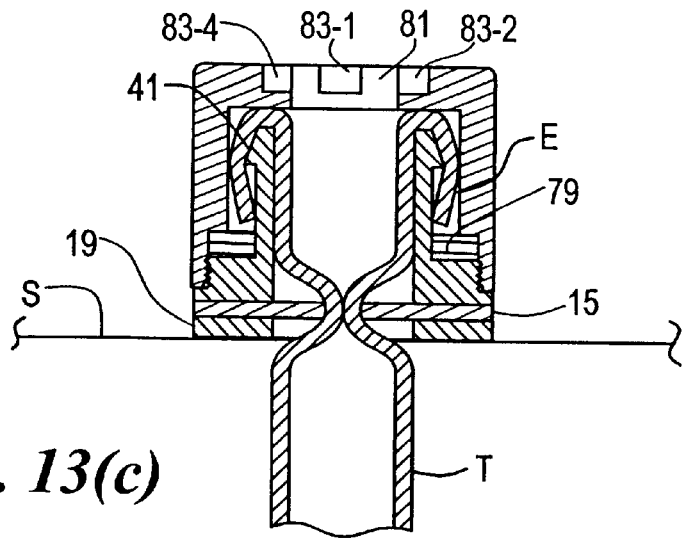

Referring now to FIGS. 13(a) through 13(c), adaptor 11 and tube T are shown with clamp 15 in its closed position. As can be seen, the positioning of tube T within slit 59 causes tube T to be compressed or pinched to an extent that fluid cannot flow therethrough. Consequently, said pinching or compression of tube T effectively acts as a valve to prevent the escape of gastric fluids from the patient.

Figure 13D:
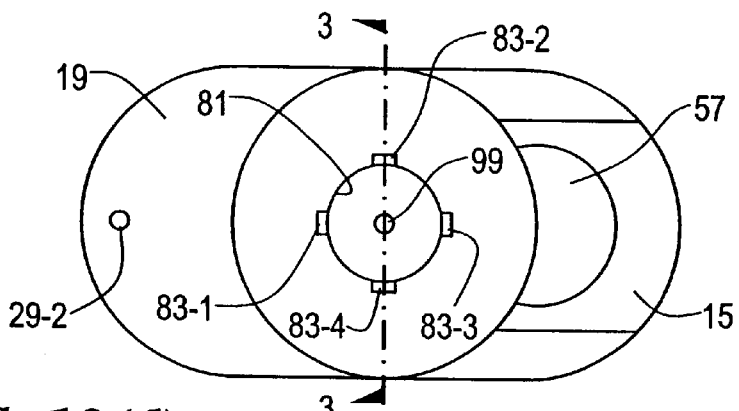
FIG. 13(d) is a top view of the adaptor and gastrostomy feeding tube of FIG. 13(a), with a guide wire being held within the closed gastrostomy feeding tube.
Figure 13E:
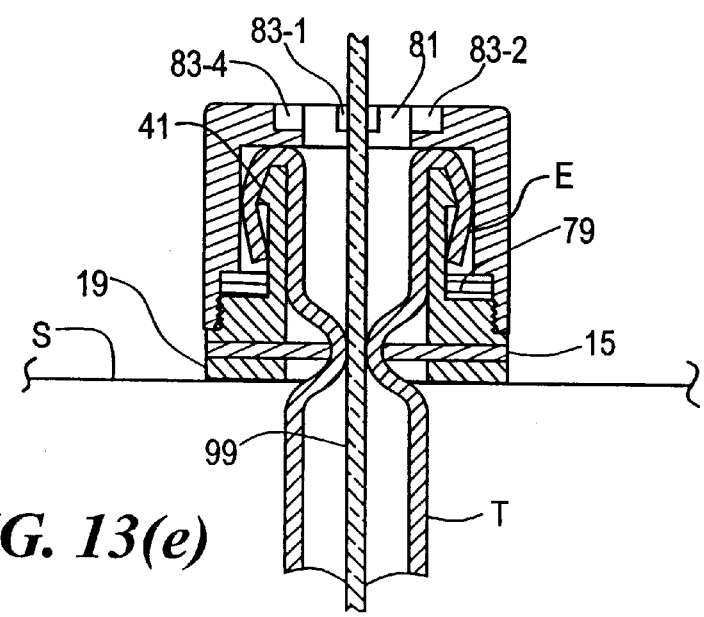
FIG. 13(e) is a section view of the adaptor, implanted gastrostomy feeding tube and guide wire of FIG. 13(d) taken along line 3—3.

Referring now to FIGS. 13(d) and 13(e), it can be seen that a guide wire 99 can be securely held in place by tube T by inserting said guide wire 99 through tube T and then positioning clamp 15 in its closed position. Such a guide wire could be used, for example, for placement of a catheter into the gastrointestinal tract. Instead of using guide wire 99, a catheter could be used, for example, to deliver a dye or medication or to perform diagnostic and/or interventional procedures.

As can be appreciated, adaptor 11 possesses a number of significant features, some of which are not possessed by existing adaptors for gastrostomy feeding tubes. One such feature is that adaptor 11 permits a tube to be attached thereto by inserting the proximal end of the tube up through the body of the adaptor and then folding the proximal end of the tube down over the top of the adaptor body, thereby obviating the need for the operator to hold the tube from below the adaptor when securing the tube to the adaptor. Another feature is that adaptor 11 is secured to the gastrostomy feeding tube in a 360 degree manner. This minimizes the chance that an uneven distribution of retentive force will be applied to the tube, causing the tube to tear. Another such feature is that adaptor 11 is capable of being detached from and then re-attached to the tube, thereby permitting the length of the tube to be adjusted and/or permitting the adaptor and tube to be cleaned of debris. Still another feature, noted above, is that adaptor 11 retains the tube with a considerable retentive force. Specifically, adaptor 11 is able to withstand a pulling force of approximately 18 pounds without compromising the quality of the seal between the tube and the adaptor 11. Still yet another feature is that the cap 17 is designed to be screwed and/or unscrewed with a mating tool. This minimizes the possibility that the patient will inadvertently unscrew cap 17. Still a further feature is that a manual valve is employed to open and close the tube, said manual valve permitting the tube to have its full inner diameter when in its open state. This maximizes the amount of food and/or medications that can be delivered and minimizes the possibility that the tube will become clogged. Still yet a further feature is that no part of the adaptor is inserted below the skin surface, thereby allowing the stoma tract created in the patient to be kept at its minimum size. Still even a further feature is that a delivery tube/connector can be coupled to the gastrostomy feeding tube while the adaptor is in its closed position and that the adaptor can be switched from its open position to its closed position before removing the delivery tube/connector therefrom. This prevents spills, leakage and/or gastric reflux of stomach contents. Still even yet a further feature is that the delivery tube/connector can be inserted directly into the gastrostomy feeding tube, with the gastrostomy feeding tube forming a seal directly around the delivery tube/connector. This reduces the number of parts required.

Although adaptor 11 has been described herein in the context of low profile use with a gastrostomy feeding tube, it should be understood that adaptor 11 is not limited to low profile use and could be used with a gastrostomy feeding tube in a high profile arrangement. Moreover, apart from whether adaptor is used in a low profile or high profile context, adaptor 11 is not limited to use with gastrostomy feeding tubes and may be used with various other medical catheters, including drainage catheters.

Figure 14:
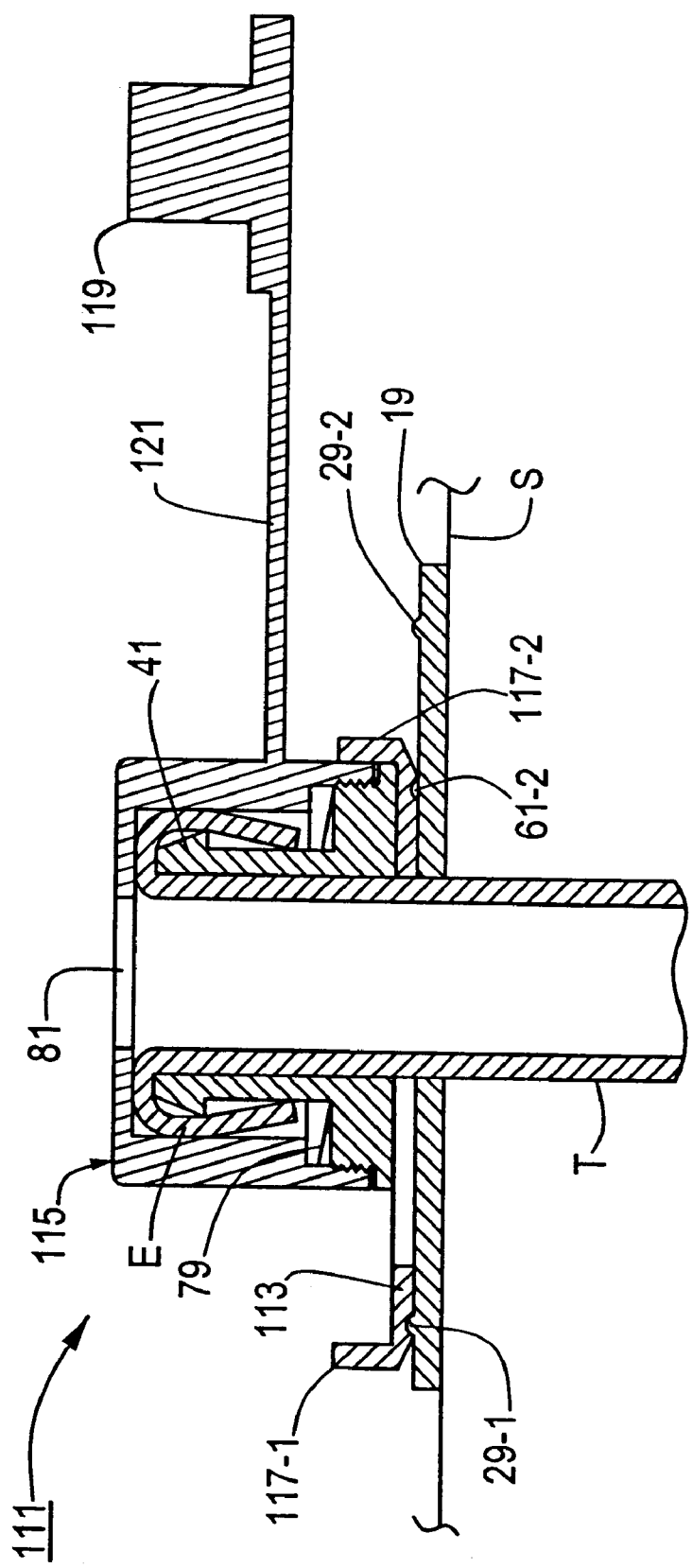
FIG. 14 is a section view off a second embodiment of a low profile adaptor constructed according to the teachings of the present invention for use with a medical catheter, said adaptor being shown secured to the proximal end of an implanted gastrostomy feeding tube.

Referring now to FIG. 14, there is shown a section view of a second embodiment of a low profile adaptor constructed according to the teachings of the present invention for use with a medical catheter, said adaptor being shown secured to the proximal end of an implanted gastrostomy feeding tube and being represented generally by reference numeral 111.

Adaptor 111 is similar in many respects to adaptor 11, the principal differences between adaptor 111 and adaptor 11 being that clamp 15 and cap 17 of adaptor 11 are replaced with a clamp 113 and a cap 115, respectively, in adaptor 111.

Clamp 113 is identical to clamp 15, except that clamp 113 has a pair of ends 117-1 and 117-2 that are angled upwardly to facilitate the grasping and sliding of clamp 113 relative to body 13.

Cap 115 is similar in many respects to cap 17, the principal differences between cap 115 and cap 17 being that (i) cap 115 does not include recesses 83-1 through 83-4 of cap 17; and (ii) cap 115 further includes a plug 119 connected by a strap 121 to side wall 75, plug 119 being appropriately dimensioned for removable insertion through opening 81 and into tube T in such a way as to seal shut tube T when inserted thereinto.

Adaptor 111 may be secured to a gastrostomy feeding tube T in much the same manner as described above for adaptor 11. In addition, once secured to a gastrostomy feeding tube T, adaptor 111 may be used in same manner as adaptor 11, with one notable exception—tube T may be closed by sliding clamp 113 from its open position to its closed position and/or by inserting plug 119 into tube T through its proximal end E.

In view of the similar functions performed by clamp 113 and plug 119, it can readily be appreciated that adaptor 111 could be modified so as to omit one of plug 119 and clamp 113 therefrom.

Figure 15:
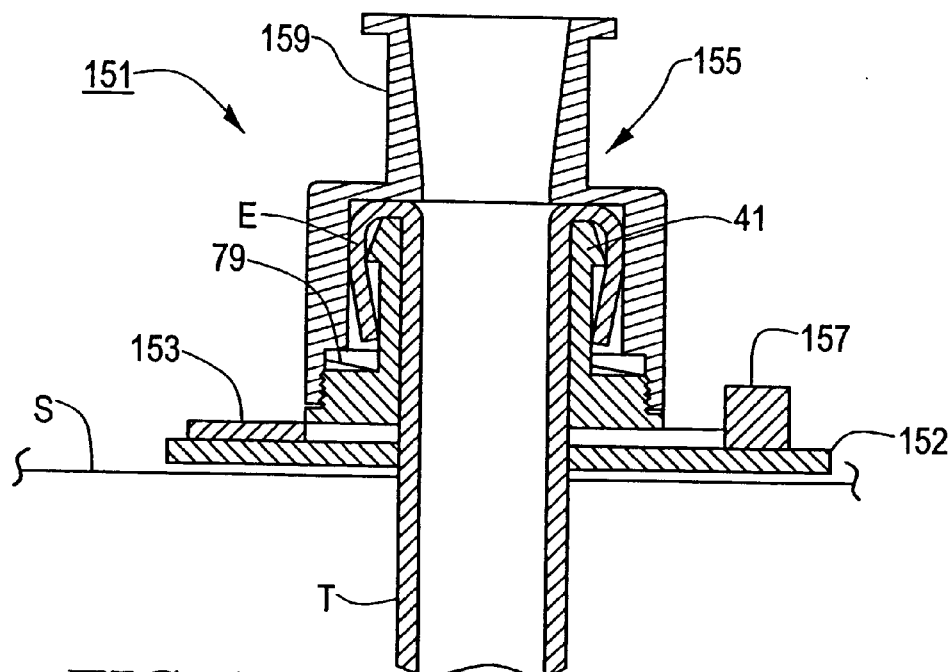
FIG. 15 is a section view of a third embodimient of a low profile adaptor constructed according to the teachings of the present invention for use with a medical catheter, said adaptor being shown secured to the proximal end of an implanted gastrostomy feeding tube.

Referring now to FIG. 15, there is shown a section view of a third embodiment of a low profile adaptor constructed according to the teachings of the present invention for use with a medical catheter, said adaptor being shown secured to the proximal end of an implanted gastrostomy feeding tube and being represented generally by reference numeral 151.

Adaptor 151 is similar in many respects to adaptor 11, the principal differences between adaptor 151 and adaptor 11 being that base 19, clamp 15 and cap 17 of adaptor 11 are replaced with a base 152, a clamp 153 and a cap 155, respectively, in adaptor 151.

Base 152 is identical to base 19, except that base 152 does not include detents 29-1 and 29-2.

Clamp 153 is similar to clamp 15, except that clamp 153 (i) has an upward projection 157 formed at one end thereof to facilitate the grasping and sliding of clamp 153 relative to body 13 and (ii) does not include recesses 61-1 and 61-2.

Cap 155 is similar in many respects to cap 17, the principal differences between cap 155 and cap 17 being that (i) cap 155 does not include recesses 83-1 through 83-4 of cap 17 and (ii) cap 155 further includes a fitting 159 for receiving a medical luer.

Figure 16:
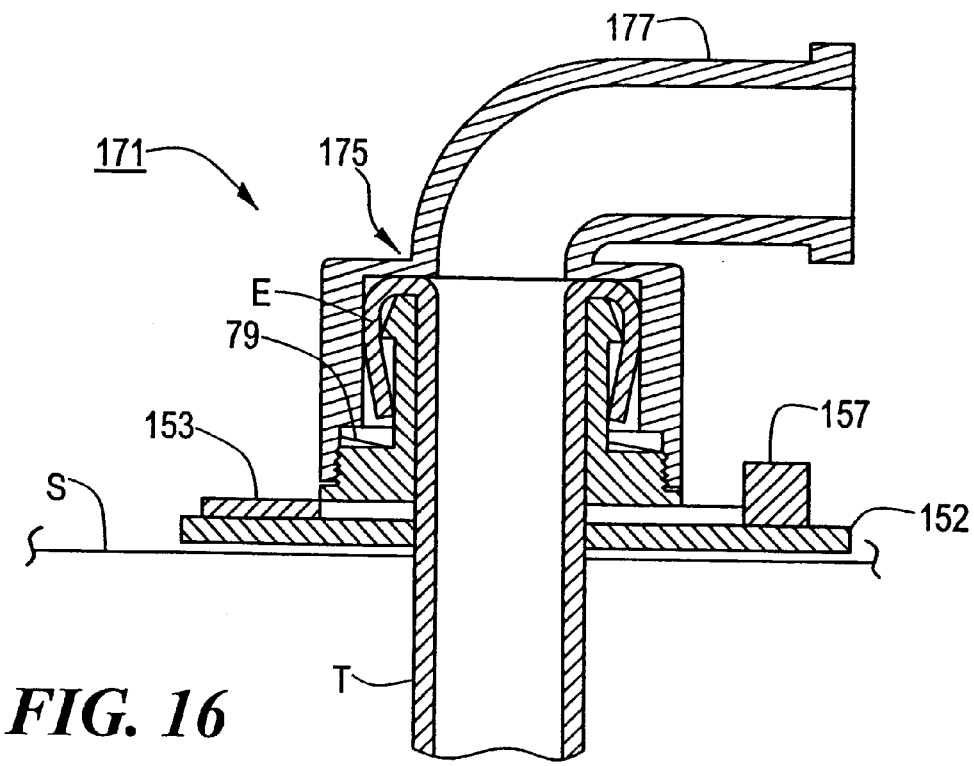
FIG. 16 is a section view of a fourth embodiment of a low profile adaptor constructed according to the teachings of the present invention for use with a medical catheter, said adaptor being shown secured to the proximal end of an implanted gastrostomy feeding tube.

Referring now to FIG. 16, there is shown a section view of a fourth embodiment of a low profile adaptor constructed according to the teachings of the present invention for use with a medical catheter, said adaptor being shown secured to the proximal end of an implanted gastrostomy feeding tube and being represented generally by reference numeral 171.

Adaptor 171 is similar in many respects to adaptor 151, the principal difference between adaptor 171 and adaptor 151 being that cap 155 of adaptor 151 is replaced with a cap 175 in adaptor 171. Cap 175 has a fitting 177 angled 90 degrees relative to the longitudinal axis of tube T.

Referring now to FIGS. 17(a) and 17(b), there are shown a top view in an open position and a top view in a closed position, respectively, of a fifth embodiment of a low profile adaptor constructed according to the teachings of the present invention for use with a medical catheter, said adaptor being represented generally by reference numeral 201. (For purposes of explication, certain elements essential to a discussion of adaptor 201 but not otherwise visible in a top view are shown herein using dotted lines.)

Adaptor 201 is similar in many respects to adaptor 11, the principal differences between adaptor 201 and adaptor 11 being that body 13, clamp 15 and cap 17 of adaptor 11 are replaced with a body 203, a pair of clamps 205-1 and 205-2 and a cap 207, respectively, in adaptor 111.

Body 203 is similar in most respects to body 13, the principal differences between body 203 and body 13 being that body 203 (i) does not include detents 29-1 and 29-2 and (ii) has a transverse slot 209 that is wider than transverse slot 39 of body 13.

Clamps 205-1 and 205-2, which extend through slot 209, are pivotally mounted on body 203 at their respective first ends 211-1 and 211-2 with pegs 213-1 and 213-2, respectively, and are detachably engageable with one another at their respective second ends 215-1 and 215-2 with a ratchet-type mechanism.

Cap 207 is virtally identical to cap 17, the principal difference between cap 207 and cap 17 being that cap 207 does not include recesses 83-1 through 83-4 of cap 17.

As can be seen in FIG. 17(a), when clamps 205-1 and 205-2 are positioned so that their respective second ends 215-1 and 215-2 are pivoted away from one another, clamps 205-1 and 205-2 do not pass through bore 37 and, therefore, do not apply any compressive force to a tube (not shown) positioned therewithin. Consequently, such a tube within bore 37 is able to occupy its full inner diameter. By contrast, as can be seen in FIG. 17(b), when clamps 205-1 and 205-2 are positioned so that their respective second ends 215-1 and 215-2 are brought into engagement with one another, a tube (not shown) positioned within bore 37 is pinched shut between clamps 205-1 and 205-2.

Referring now to FIGS. 18(a) and 18(b), there are shown a top view in an open position and a top view in a closed position, respectively, of a sixth embodiment of a low profile adaptor constructed according to the teachings of the present invention for use with a medical catheter, said adaptor being represented generally by reference numeral 221. (For purposes of explication, certain elements essential to a discussion of adaptor 221 but not otherwise visible in a top view are shown herein using dotted lines.)

Adaptor 221 is similar in many respects to adaptor 201, the principal differences between adaptor 221 and adaptor 201 being that clamps 205-1 and 205-2 of adaptor 201 are replaced with a single clamp 223 in adaptor 221.

Clamp 223, which extends through slot 209, is pivotally mounted on body 203 at a first end 225 with a peg 227. The second end 229 of clamp 223 is detachably engageable with a post 230 secured to body 203.

As can be seen in FIG. 18(a), when clamp 223 is positioned so that its second end 229 is pivoted away from post 230, clamp 223 does not extend through bore 37 and no lateral compression is applied by clamp 223 to a tube (not shown) disposed within bore 37. Consequently, such a tube disposed within bore 37 is left to occupy its full inner diameter. By contrast, as can be seen in FIG. 18(b), when clamp 223 is positioned so that its second end 229 is brought into engagement with post 230, a tube (not shown) positioned within bore 37 is pinched shut between clamp 223 and the wall bounding bore 37.

Figure 19A:
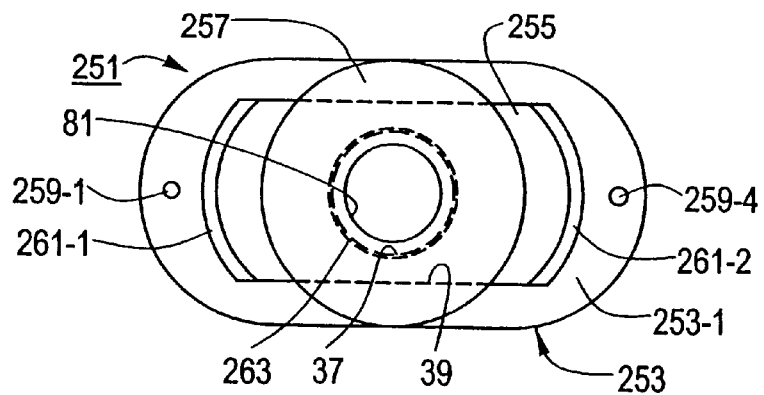
FIGS. 19(a) through 19(c) are top views, in an open position, in a first closed position and in a second closed position, respectively, of a seventh embodiment of a low profile adaptor constructed according to the teachings of the present invention for use with a medical catheter.
Figure 19B:
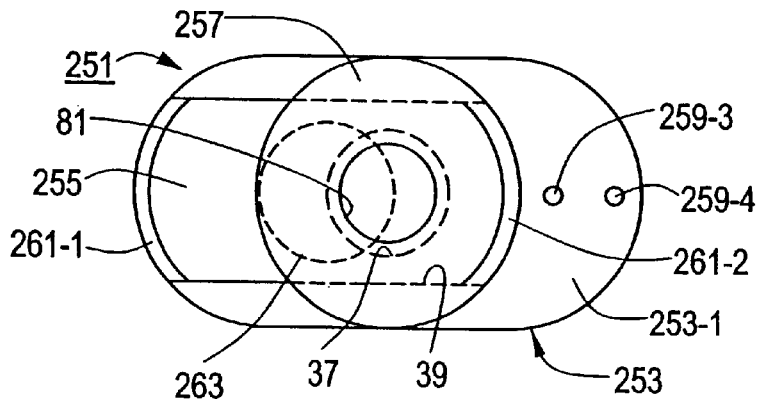
Figure 19C:
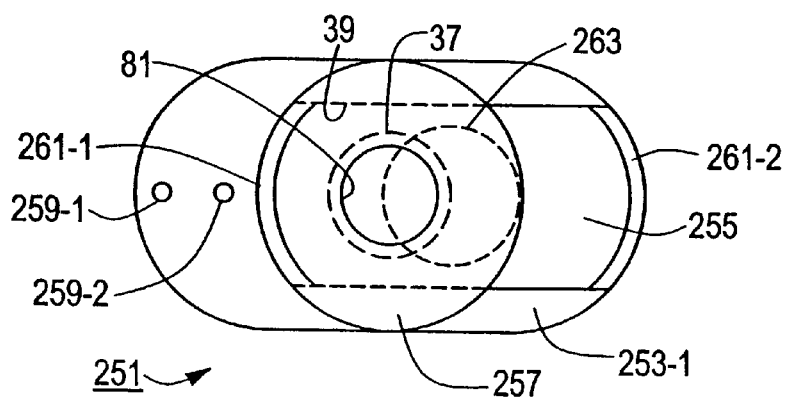

Referring now to FIGS. 19(a) through 19(c), there are shown a top view in an open position, a top view in a first closed position and a top view in a second closed position, respectively, of a seventh embodiment of a low profile adaptor constructed according to the teachings of the present invention for use with a medical catheter, said adaptor being represented generally by reference numeral 251. (For purposes of explication, certain elements essential to a discussion of adaptor 251 but not otherwise visible in a top view are shown herein using dotted lines.)

Adaptor 251 is similar in many respects to adaptor 11, the principal differences between adaptor 251 and adaptor 11 being that body 13, clamp 15 and cap 17 of adaptor 11 are replaced with a body 253, a clamp 255 and a cap 257, respectively, in adaptor 251.

Body 253 is similar in most respects to body 13, the principal difference between body 253 and body 13 being that body 253 includes four detents 259-1 through 259-4 formed on the top surface of its base 253-1 along the longitudinal centerline thereof, instead of the two detents 29-1 and 29-2 provided in body 13.

Clamp 255 is similar in many respects to clamp 15, the principal differences between clamp 255 and clamp 15 being that clamp 255 (i) has upwardly projecting ends 261-1 and 261-2 to facilitate the grasping of clamp 255 and (ii) clamp 255 has an opening 263 corresponding only to the wide circular region 57 of clamp 15. Clamp 255 also has four recesses (not shown) on its bottom surface for alternatively engaging detents 259-1 and 259-2, detents 259-2 and 259-3 or detents 259-3 and 259-4.

Cap 257 is virtually identical to cap 17, the principal difference between cap 257 and cap 17 being that cap 257 does not include recesses 83-1 through 83-4 of cap 17.

As can be seen in FIG. 19(a), when clamp 255 is positioned so that its opening 263 is aligned with bore 37, no lateral compression is applied by clamp 223 to a tube (not shown) disposed within bore 37. Consequently, such a tube disposed within bore 37 is left to occupy its full inner diameter. By contrast, as can be seen in FIG. 19(b) or 19(c), when clamp 255 is positioned so that opening 263 is moved out of alignment with bore 37, a tube (not shown) positioned within bore 37 is pinched shut between clamp 255 and the wall bounding bore 37.

One advantageous feature of adaptor 251 is that it has two closed positions which are on opposite sides of its open position; consequently, adaptor 251 may be particularly well-suited for both right-handed and left-handed users.

Figure 20A:
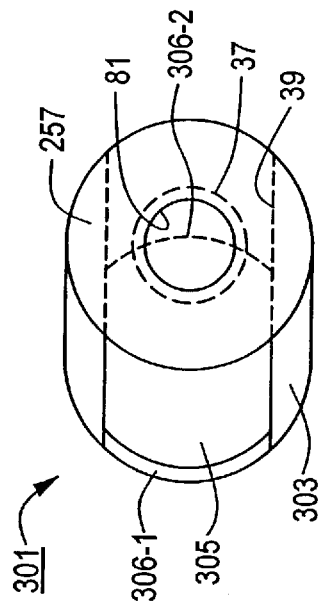
FIGS. 20(a) and 20(b) are top views, in an open position and in a closed position, respectively, of an eighth embodiment of a low profile adaptor constructed according to the teachings of the present invention for use with a medical catheter.
Figure 20B:
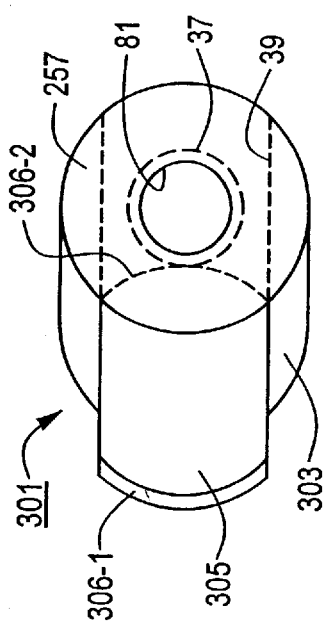

Referring now to FIGS. 20(a) and 20(b), there are shown a top view in an open position and a top view in a closed position, respectively, of an eighth embodiment of a low profile adaptor constructed according to the teachings of the present invention for use with a medical catheter, said adaptor being represented generally by reference numeral 301. (For purposes of explication, certain elements essential to a discussion of adaptor 301 but not otherwise visible in a top view are shown herein using dotted lines.)

Adaptor 301 is similar in many respects to adaptor 251, the principal differences between adaptor 301 and adaptor 251 being that body 253 and clamp 255 of adaptor 251 are replaced with a body 303 and a clamp 305, respectively, in adaptor 301.

Body 303 is similar in most respects to body 253, the principal difference between body 253 and body 303 being that body 303 does not include the right portion of base 253-1 of body 253.

Clamp 305 is similar in many respects to clamp 255, the principal differences between clamp 305 and clamp 255 being that (i) clamp 305 has an upwardly projecting left end 306-1 and a flat right end 306-2 and (ii) clamp 305 is truncated in length so that its right end 306-2 can only be advanced partially across bore 37.

As can be seen in FIG. 20(a), when clamp 305 is moved to its open position, right end 306-2 does not penetrate bore 37. Therefore, no lateral compression is applied by clamp 305 to a tube (not shown) disposed within bore 37, and such a tube is left to occupy its full inner diameter. By contrast, as can be seen in FIG. 20(b), when clamp 305 is moved to its closed position, right end 306-2 is moved into bore 37, thereby compressing to closure a tube (not shown) positioned within bore 37.

Figure 21A:
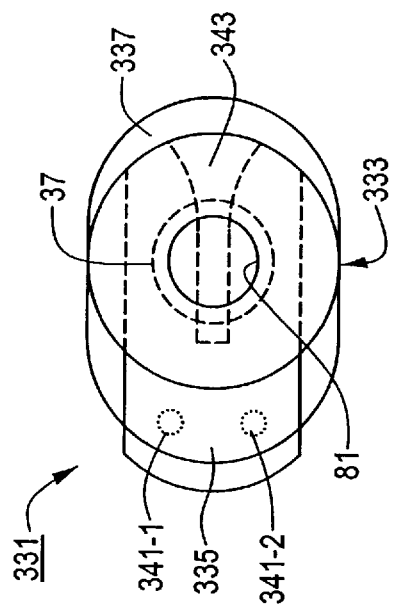
FIGS. 21(a) and 21(b) are top views, in an open position and in a closed position, respectively, of ninth embodiment of a low profile adaptor constructed according to the teachings of the present invention for use with a medical catheter.
Figure 21B:
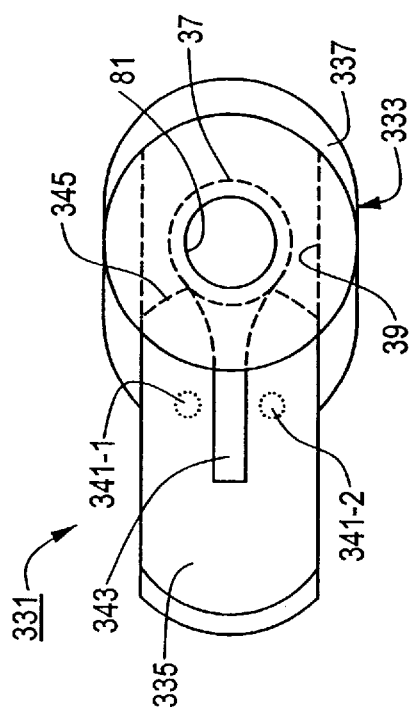

Referring now to FIGS. 21(a) and 21(b), there are shown a top view in an open position and a top view in a closed position, respectively, of an ninth embodiment of a low profile adaptor constructed according to the teachings of the present invention for use with a medical catheter, said adaptor being represented generally by reference numeral 331. (For purposes of explication, certain elements essential to a discussion of adaptor 331 but not otherwise visible in a top view are shown herein using dotted lines.)

Adaptor 331 is similar in many respects to adaptor 301, the principal differences between adaptor 331 and adaptor 301 being that body 303 and clamp 305 of adaptor 301 are replaced with a body 333 and a clamp 335, respectively, in adaptor 331.

Body 333 is similar in most respects to body 303, the principal differences between body 333 and body 303 being (i) that body 333 has a base 337 that extends both to the right and to the left of slot 39 and (ii) that a pair of detents 341-1 and 341-2 spaced equidistantly from the longitudinal centerline of base 337 are formed on the left side of base 337.

Clamp 335 is similar in many respects to clamp 305, the principal differences between clamp 335 and clamp 305 being that (i) clamp 335 is provided with a slit 343 that extends from approximately its midpoint to its right end 345 and (ii) clamp 335 is sized to extend all the way across bore 37 when moved to its closed position. Clamp 335 is also provided with two sets of recesses (not shown) for receiving detents 341-1 and 341-2 when clamp 335 is placed in its open and closed positions.

As can be seen in FIG. 21(a), when clamp 335 is moved to its open position, right end 345 does not penetrate bore 37. Therefore, no lateral compression is applied by clamp 335 to a tube (not shown) disposed within bore 37, and such a tube is left to occupy its full inner diameter. By contrast, as can be seen in FIG. 21(b), when clamp 335 is moved to its closed position, slit 343 intersects bore 37, thereby compressing to closure a tube (not shown) positioned within bore 37.

Referring now to FIGS. 22(a) and 22(b), there are shown a top view in an open position and a top view in a closed position, respectively, of a tenth embodiment of a low profile adaptor constructed according to the teachings of the present invention for use with a medical catheter, said adaptor being represented generally by reference numeral 351. (For purposes of explication, certain elements essential to a discussion of adaptor 351 but not otherwise visible in a top view are shown herein using dotted lines.)

Adaptor 351 is similar in many respects to adaptor 331, the principal differences between adaptor 351 and adaptor 331 being that body 333 and clamp 335 of adaptor 331 are replaced with a body 353 and a pair of clamps 355-1 and 355-2, respectively, in adaptor 351.

Body 353 is similar in most respects to body 333, the principal differences between body 353 and body 333 being (i) that body 353 has a base whose right and left portions 357-1 and 357-2, respectively, are equal in size to one another and (ii) that a first pair of detents 359-1 and 359-2 are formed on left portion 357-1 and a second pair of detents 361-1 and 361-2 are formed on right portion 357-2.

Clamps 355-1 and 355-2 are similar in some respects to clamp 335, the principal differences between the respective clamps being that clamps 355-1 and 355-2 are slidably mounted to enter slot 39 from opposite ends thereof and are sized and shaped so as to form a narrow slit 363 when brought together.

As can be seen in FIG. 22(a), when clamps 355-1 and 355-2, are moved to their open positions, their inside ends 365-1 and 365-2 do not penetrate bore 37. Therefore, no lateral compression is applied by clamp 355-1 and 355-2 to a tube (not shown) disposed within bore 37, and such a tube is left to occupy its full inner diameter. By contrast, as can be seen in FIG. 22(b), when clamps 355-1 and 355-2 are moved together to their closed positions, slit 363 is formed, slit 363 intersecting bore 37 so as to compress to closure a tube (not shown) positioned within bore 37.

Referring now to FIGS. 23(a) and 23(b), there are shown a top view in an open position and a top view in a closed position, respectively, of an eleventh embodiment of a low profile adaptor constructed according to the teachings of the present invention for use with a medical catheter, said adaptor being represented generally by reference numeral 381. (For purposes of explication, certain elements essential to a discussion of adaptor 381 but not otherwise visible in a top view are shown herein using dotted lines.)

Adaptor 381 is similar in many respects to adaptor 301, the principal differences between adaptor 381 and adaptor 301 being that body 303 and clamp 305 of adaptor 301 are replaced with a body 383 and a clamp 385, respectively, in adaptor 381.

Body 383 is similar in many respects to body 303, the principal difference between the two bodies being that body 383 does not include a base portion.

Clamp 385 is similar in certain respects to clamp 305, the principal difference between the two clamps being that clamp 385 is a generally U-shaped member having a pair of outwardly biasing legs 387-1 and 387-2 connected by a curved end portion 389. A first pair of notches 391-1 and 391-2 are provided in legs 387-1 and 387-2, respectively, for receiving a corresponding pair of barbs 393-1 and 393-2 formed on body 383 to maintain clamp 385 in a closed position within slot 39, and a second pair of notches 395-1 and 395-2 are provided in legs 387-1 and 387-2, respectively, for receiving barbs 393-1 and 393-2, respectively, to maintain clamp 385 in an open position within slot 39. To disengage barbs 393-1 and 393-2 from notches 391-1 and 391-2 or notches 395-1 and 395-2, one pivots legs 387-1 and 387-2 towards one another.

As can be seen in FIG. 23(a), when clamp 385 is moved to its open position, end portion 389 does not penetrate bore 37. Therefore, no lateral compression is applied by clamp 385 to a tube (not shown) disposed within bore 37, and such a tube is left to occupy its full inner diameter. By contrast, as can be seen in FIG. 23(b), when clamp 385 is moved to its closed position, end portion 389 intersects bore 37 so as to compress to closure a tube (not shown) positioned within bore 37.

Figure 24B:
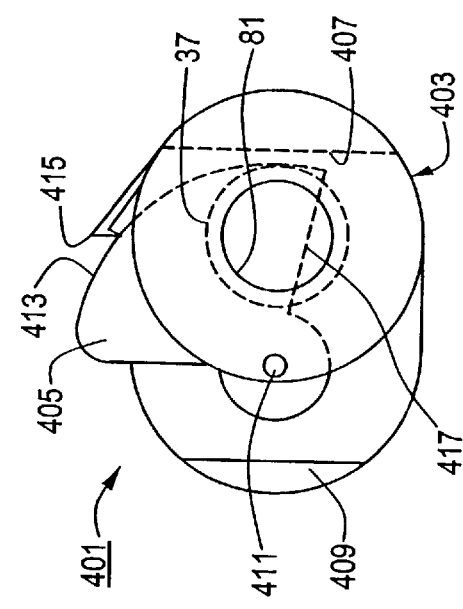
FIGS. 24(a) and 24(b) are top views, in an open position and in a closed position, respectively, of a twelfth embodiment of a low profile adaptor constructed according to the teachings of the present invention for use with a medical catheter.
Figure 24A:
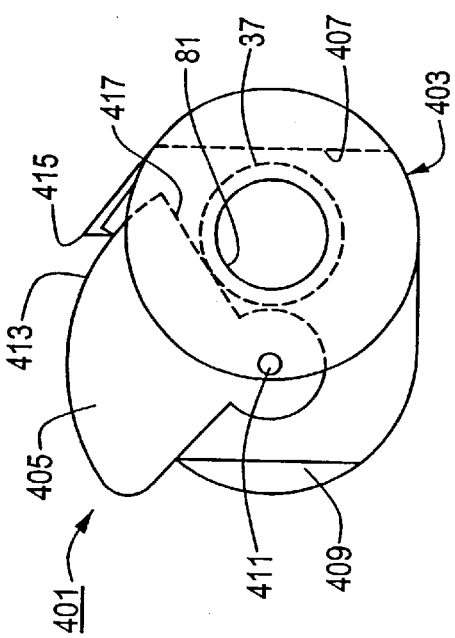

Referring now to FIG. 24(a) and 24(b), there are shown a top view in an open position and a top view in a closed position, respectively, of a twelfth embodiment of a low profile adaptor constructed according to the teachings of the present invention for use with a medical catheter, said adaptor being represented generally by reference numeral 401. (For purposes of explication, certain elements essential to a discussion of adaptor 401 but not otherwise visible in a top view are shown herein using dotted lines.)

Adaptor 401 is similar in many respects to adaptor 301, the principal differences between adaptor 401 and adaptor 301 being that body 303 and clamp 305 of adaptor 301 are replaced with a body 403 and a clamp 405, respectively, in adaptor 401.

Body 403 is similar in many respects to body 303, the principal difference between the two bodies being that body 403 comprises a transverse slot 407 that is oriented transverse to the longitudinal axis of base 409, as opposed to being parallel to the longitudinal axis of base 409. No detents are formed on base 409.

Clamp 405 differs from clamp 305 in that clamp 405 is a fan-shaped member pivotally mounted within slot 407 on a peg 411. A plurality of teeth (not shown) are formed along an edge 413 of clamp 405, said teeth being engageable in a ratchet-type manner by a pawl 415 pivotally mounted on body 403.

As can be seen in FIG. 24(a), when clamp 405 is moved to its open position, the leading edge 417 of clamp 405 does not penetrate bore 37. Therefore, no lateral compression is applied by clamp 405 to a tube (not shown) disposed within bore 37, and such a tube is left to occupy its full inner diameter. By contrast, as can be seen in FIG. 24(b), when clamp 405 is moved to its closed position, leading edge 417 intersects bore 37 so as to compress to closure a tube (not shown) positioned within bore 37.

Figure 25B:
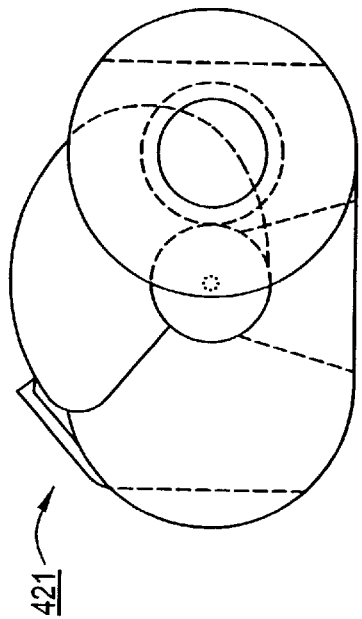
FIGS. 25(a) and 25(b) are top views, in an open position and in a closed position, respectively, of a thirteenth embodiment of a low profile adaptor constructed according to the teachings of the present invention for use with a medical catheter.
Figure 25A:
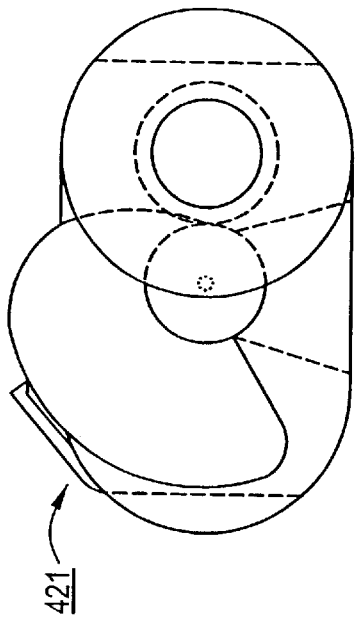

An alternative embodiment to adaptor 401 is shown in FIGS. 25(a) and 25(b) and is represented generally therein by reference numeral 421.

It should be noted that adaptors 401 and 421, in addition to being positionable in an open position and a closed position, may also be positioned in a plurality of partially open positions located between said open position and said closed position. (It should also be noted that several of the other adaptors described above could be modified to additionally be positionable in one or more partially open positions. For example, adaptor 11 could be modified to include additional detents 29 appropriately positioned along the longitudinal axis of base 19.)

Figure 26A:
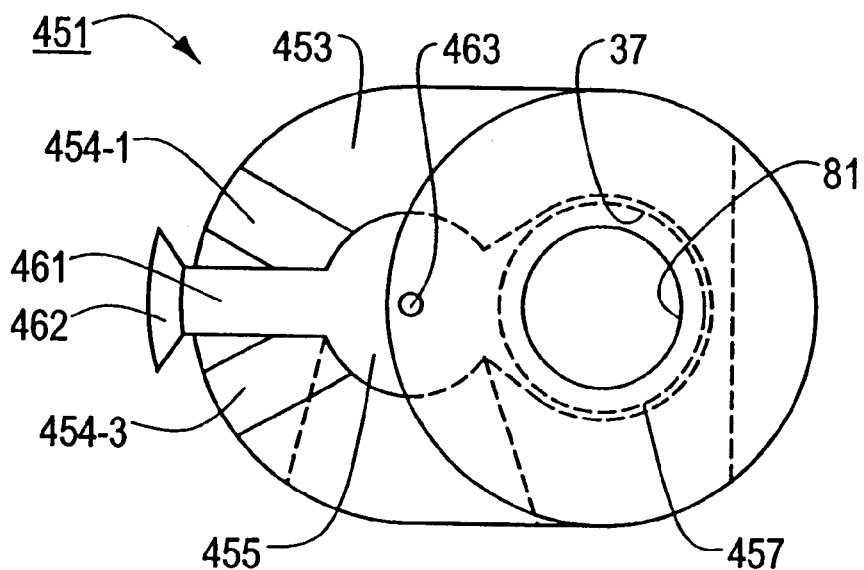
FIGS. 26(a) and 26(b) are top views, in an open position and in a closed position, respectively, of a fourteenth embodiment of a low profile adaptor constructed according to the teachings of the present invention for use with a medical catheter.
Figure 26B:
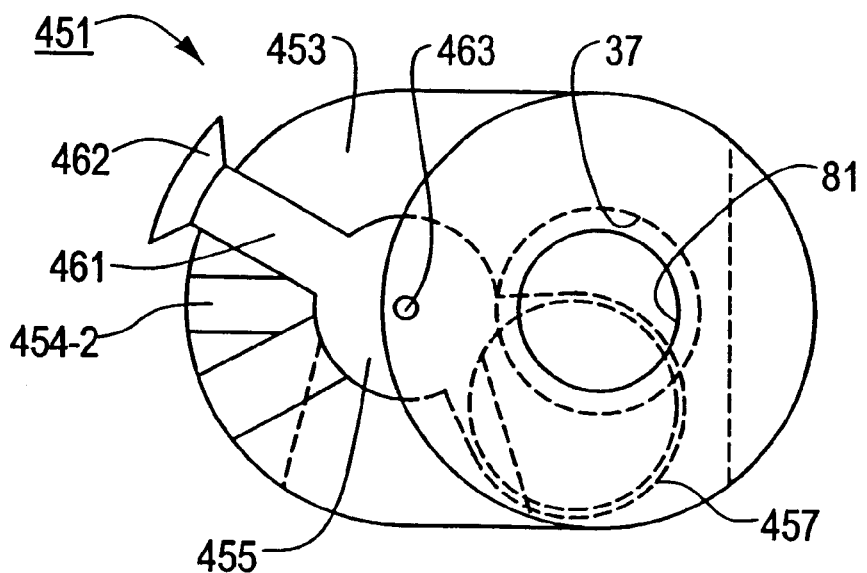

Referring now to FIGS. 26(a) and 26(b), there are shown a top view in an open position and a top view in a closed position, respectively, of a fourteenth embodiment of a low profile adaptor constructed according to the teachings of the present invention for use with a medical catheter, said adaptor being represented generally by reference numeral 451. (For purposes of explication, certain elements essential to a discussion of adaptor 451 but not otherwise visible in a top view are shown herein using dotted lines.)

Adaptor 451 is similar in many respects to adaptor 401, the principal differences between adaptor 451 and adaptor 401 being that body 403 and clamp 405 of adaptor 401 are replaced with a body 453 and a clamp 455, respectively, in adaptor 451.

Body 453 is similar in many respects to body 403, some of the more notable differences between the two bodies being that body 453 comprises a plurality of grooves 454-1 through 454-3, the purpose of which will become apparent below.

Clamp 455 is similar in certain respects to clamp 405, the principal difference between the two clamps being that clamp 455 is an elongated member having a first end shaped to include an aperture 457 and a second end 461 terminating with a handle 462, aperture 457 being sized and shaped to correspond to bore 37. Clamp 455 is pivotally mounted at an intermediate point thereon with a peg 463 and is movable between (i) a first position in which aperture 457 is aligned with bore 37 and second end 461 is seated within groove 454-2, (ii) a second position in which aperture 457 is only partially aligned with bore 37 and second end 461 is seated within groove 454-1, and (iii) a third position in which aperture 457 is only partially aligned with bore 37 and second end 461 is seated within groove 454-3.

As can be seen in FIG. 26(a), when clamp 455 is moved to its open position, aperture 457 is aligned with bore 37. Therefore, no lateral compression is applied by clamp 455 to a tube (not shown) disposed within bore 37, and such a tube is left to occupy its full inner diameter. By contrast, as can be seen in FIG. 26(b), when clamp 455 is moved to one its two closed positions, aperture 457 only partially overlaps with bore 37. This cause a tube (not shown) positioned within bore 37 to be compressed to closure.

Figure 27:
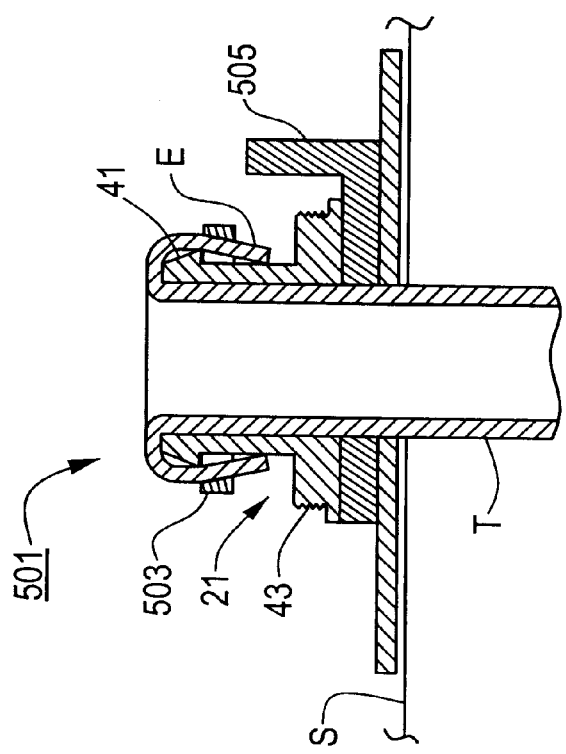
FIG. 27 is a section view of a fifteenth embodiment of a low profile adaptor constructed according to the teachings of the present invention for use with a medical catheter, said adaptor being shown secured to the proximal end of an implanted gastrostomy feeding tube.

Referring now to FIG. 27, there is shown a section view of a fifteenth embodiment of a low profile adaptor constructed according to the teachings of the present invention for use with a medical catheter, said adaptor being shown secured to the proximal end of an implanted gastrostomy feeding tube and being represented generally by reference numeral 501.

Adaptor 501 is similar in many respects to adaptor 11, the principal differences between adaptor 11 and adaptor 501 being that adaptor 501 (i) does not include cap 17, but rather, includes an elastic band 503 for securing proximal end E of tube T to the exterior of sleeve 21 (including barb 41); and (ii) does not include clamp 13, but rather, includes a pivotally mounted clamp 505 movable between an open position in which tube T is left to occupy its full inner diameter and a closed position in which tube T is pinched shut.

It should be understood that elastic band 503 could be replaced with a cable tie or other similar mechanism for securing the proximal end E of tube T to the exterior of sleeve 21.

It should also be understood that, although sleeve 21 is shown in the present embodiment having thread 43, thread 43 is not utilized in said embodiment and could be eliminated.

Figure 28:
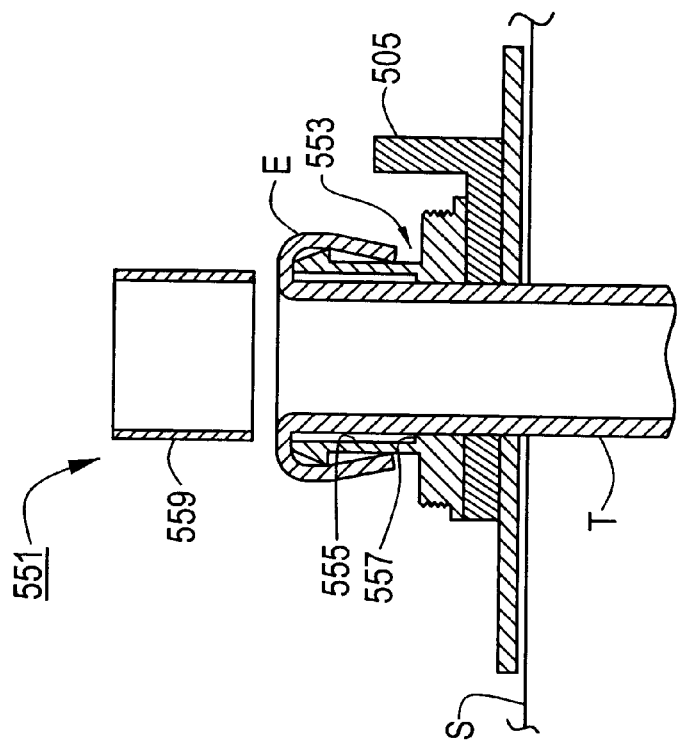
FIG. 28 is a partially exploded section view of sixteenth embodiment of a low profile adaptor constructed according to the teachings of the present invention for use with a medical catheter, said adaptor being shown secured to the proximal end of an implanted gastrostomy feeding tube.

Referring now to FIG. 28, there is shown a partially exploded section view of a sixteenth embodiment of a low profile adaptor constructed according to the teachings of the present invention for use with a medical catheter, said adaptor being shown secured to the proximal end of an implanted gastrostomy feeding tube and being represented generally by reference numeral 551.

Adaptor 551 is similar in most respects to adaptor 501, the principal differences between adaptor 551 and adaptor 501 being (i) that adaptor 551 includes a sleeve 553 whose upper portion 555 has an increased inside diameter terminating in a shelf 557 and (ii) that adaptor 551 does not include band 503, but rather, includes a tubular insert 559 adapted for insertion into the gastrostomy feeding tube T until resting upon shelf 557. In this manner, insert 559 wedges the proximal end E of tube T against the inside of sleeve 553.

Figure 29:
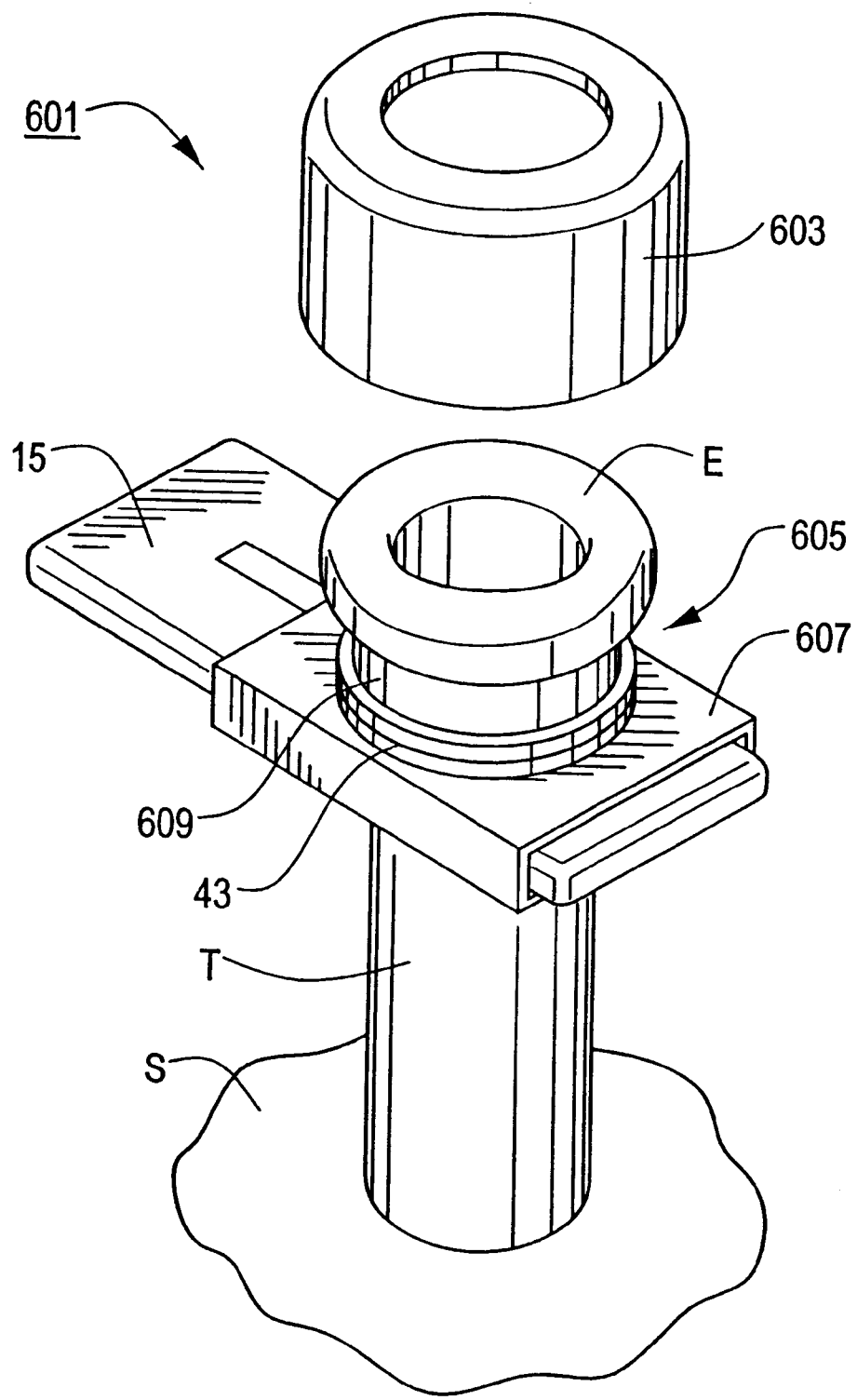
FIG. 29 is a partially exploded section view of a seventeenth embodiment of a low profile adaptor constructed according to the teachings of the present invention for use with a medical catheter, said adaptor being shown secured to the proximal end of an implanted gastrostomy feeding tube.

Referring now to FIG. 29, there is shown a partially exploded section view of a seventeenth embodiment of a low profile adaptor constructed according to the teachings of the present invention for use with a medical catheter, said adaptor being shown secured to the proximal end of an implanted gastrostomy feeding tube and being represented generally by reference numeral 601.

Adaptor 601 is similar in many respects to adaptor 11. One difference between adaptor 601 and adaptor 11 is that adaptor 601 includes a cap 603 that does not include recesses 83-1 through 83-4. Another difference between adaptor 601 and adaptor 11 is that adaptor 601 includes a body 605, body 605 having a base 607 and a sleeve 609, clamp 15 being slidably mounted within base 607.

It should be understood that, instead of being slidably mounted within base 607, clamp 15 could be positioned below base 607.

The embodiments of the present invention described above are intended to be merely exemplary and those skilled in the art shall be able to make numerous variations and modifications to it without departing from the spirit of the present invention. All such variations and modifications are intended to be within the scope of the present invention as defined in the appended claims.

What is claimed is:

1. An adaptor well-suited for use with a medical catheter, the medical catheter having a proximal end, said adaptor comprising:
   (a) a sleeve, said sleeve having a longitudinal bore up through which the proximal end of the medical catheter may be inserted;
   (b) means for securing the medical catheter to said sleeve; and
   (c) means for alternately opening and closing the medical catheter to the passage of fluid therethrough.

2. The adaptor as claimed in claim 1 further comprising a base, said sleeve extending upwardly from said base, said base having a transverse opening aligned with said longitudinal bore.

3. The adaptor as claimed in claim 1 wherein said sleeve includes an external barb over which the proximal end of the medical catheter may be inverted.

4. The adaptor as claimed in claim 1 wherein said sleeve further comprises a transverse slot, said transverse slot intersecting said longitudinal bore, and wherein said alternately opening and closing means comprises a clamp movable within said transverse slot between a first position in which said clamp compresses to closure the medical catheter and a second position in which said clamp does not compress the medical catheter.

5. The adaptor as claimed in claim 4 wherein said clamp is slidably mounted within said transverse slot and has a transverse opening, said transverse opening having a wide circular portion and a narrow slit portion, said narrow slit portion being aligned with said longitudinal bore of said sleeve in said first position, said wide circular portion being aligned with said longitudinal bore in said second position.

6. The adaptor as claimed in claim 4 wherein said clamp is slidably mounted within said transverse slot and has a transverse opening, said transverse opening being only partially aligned with said longitudinal bore of said sleeve in said first position and being fully aligned with said longitudinal bore in said second position.

7. The adaptor as claimed in claim 4 wherein said clamp is a slidably mounted within said transverse slot and has an end, said end intersecting said longitudinal bore of said sleeve in said first position and not intersecting said longitudinal bore of said sleeve in said second position.

8. The adaptor as claimed in claim 4 wherein said clamp is pivotally mounted to intersect said longitudinal bore of said sleeve in said first position and not to intersect said longitudinal bore of said sleeve in said second position.

9. The adaptor as claimed in claim 1 wherein said sleeve further comprises a transverse slot, said transverse slot intersecting said longitudinal bore, and wherein said alternately opening and closing means comprises a pair of clamps movable within said transverse slot between a first position in which said clamps jointly compress to closure the medical catheter and a second position in which said clamps do not compress the medical catheter.

10. The adaptor as claimed in claim 9 wherein each of said clamps is slidably mounted within said transverse slot and has an inside end, said inside end intersecting said longitudinal bore of said sleeve in said first position and not intersecting said longitudinal bore of said sleeve in said second position.

11. The adaptor as claimed in claim 9 wherein each of said clamps is pivotally mounted to intersect said longitudinal bore of said sleeve in said first position and not to intersect said longitudinal bore of said sleeve in said second position.

12. The adaptor as claimed in claim 2 wherein said sleeve further comprises a transverse slot, said transverse slot intersecting said longitudinal bore, and wherein said alternately opening and closing means comprises a clamp positioned on said base and movable within said transverse slot between a first position in which said clamp compresses to closure the medical catheter and a second position in which said clamp does not compress the medical catheter.

13. The adaptor as claimed in claim 12 wherein said clamp has a transverse opening, said transverse opening having a wide region through which the medical catheter may pass in a transversely uncompressed state and a narrow region through which the medical catheter may pass in a transversely compressed state.

14. The adaptor as claimed in claim 1 wherein said alternately opening and closing means comprises a plug removably insertable into the proximal end of the medical catheter.

15. The adaptor as claimed in claim 1 wherein said securing means comprises a band removably mounted around the exterior of said sleeve for securing a medical catheter therebetween.

16. The adaptor as claimed in claim 1 wherein said securing means comprises a tubular member removably inserted into said sleeve for securing a medical catheter therebetween.

17. The adaptor as claimed in claim 1 wherein said securing means comprises a cap removably mounted onto said sleeve, said cap having an opening at its top end for insertion of a tube therethrough.

18. The adaptor as claimed in claim 17 wherein said alternately opening and closing means comprises a plug removably insertable through said opening in said cap and into the proximal end of the medical catheter.

19. The adaptor as claimed in claim 18 wherein plug is connected to said cap by a strap.

20. The adaptor as claimed in claim 17 wherein said cap further has an internal thread, wherein said sleeve further has an external thread and wherein said cap is removably screwed onto said sleeve by threaded engagement of said internal thread with said external thread.

21. The adaptor as claimed in claim 20 wherein said cap further has one or more recesses adapted to receive a tool for screwing said cap onto said sleeve and for unscrewing said cap from said sleeve.

22. The adaptor as claimed in claim 2 wherein said base further comprises a transverse slot, said transverse slot intersecting said transverse opening, and wherein said alternately opening and closing means comprises a clamp slidable within said transverse slot between a first position in which said clamp compresses to closure the medical catheter and a second position in which said clamp does not compress the medical catheter.

23. The combination of a medical catheter and the adaptor of claim 1, the medical catheter having a proximal end inserted up through the longitudinal bore of said sleeve and inverted over the top of said sleeve.

24. The combination as claimed in claim 23 wherein said sleeve further has a barb, said inverted medical catheter being positioned over said barb.

25. The combination as claimed in claim 24 wherein said medical catheter is a gastrostomy feeding tube, said gastrostomy feeding tube having an internal bolster disposed at its distal end.

26. An adaptor well-suited for use with a medical catheter, the medical catheter having a proximal end, said adaptor comprising:
  (a) a body, said body having a base and a sleeve, said base having a transverse bore, said sleeve extending upwardly from said base and having a longitudinal bore and a transverse slot, said longitudinal bore being aligned with said transverse bore of said base, said transverse slot intersecting said longitudinal bore, said transverse bore of said base and said sleeve being appropriately dimensioned to permit a medical catheter to be inserted up through said transverse bore of said base and said longitudinal bore of said sleeve and then inverted over the top of said sleeve;
  (b) a clamp mounted on said base and movable within said transverse slot between a first position in which said clamp transversely compresses to closure the medical catheter and a second position in which said clamp does not transversely compress the medical catheter;
  (c) means for securing the inverted proximal end of a medical catheter to said sleeve.

27. The adaptor as claimed in claim 26 wherein said clamp comprises a slide having a transverse opening, said transverse opening having a wide region through which a medical catheter may pass uncompressed and a narrow region through which a medical catheter may pass in a compressed state.

28. The adaptor as claimed in claim 27 wherein said base has a top surface upon which are formed a first detent and a second detent and wherein said clamp has a bottom surface in which are provided a first recess and a second recess, said first detent and said first recess being positioned to align said wide region with said longitudinal bore of said sleeve, said second detent and said second recess being positioned to align said narrow region with said longitudinal bore of said sleeve.

29. The adaptor as claimed in claim 28 wherein said securing means comprises a cap removably mountable on said sleeve, said cap being provided with an opening alignable with said longitudinal bore of said sleeve.

30. The combination of a medical catheter and the adaptor of claim 29, the medical catheter extending up through said transverse bore of said base and said longitudinal bore of said sleeve, the medical catheter having a proximal end turned over the top of said sleeve and secured thereto by said cap.

31. The combination as claimed in claim 30 wherein said medical catheter is a gastrostomy feeding tube, said gastrostomy feeding tube having an internal bolster disposed at its distal end.

\* \* \* \* \*